US005602322A

United States Patent [19]
Ecker et al.

[11] Patent Number: 5,602,322
[45] Date of Patent: Feb. 11, 1997

[54] CONSTITUTITIVE TRIPLE RESPONSE GENE AND MUTATIONS

[75] Inventors: Joseph R. Ecker, Erial, N.J.; Joseph J. Kieber, LaGrange Park, Ill.

[73] Assignee: The Trustees of the University of Pennsylvania, Philadelphia, Pa.

[21] Appl. No.: 261,432

[22] Filed: Jun. 17, 1994

Related U.S. Application Data

[63] Continuation-in-part of Ser. No. 3,311, Jan. 12, 1993, Pat. No. 5,444,166, which is a continuation-in-part of Ser. No. 928,464, Aug. 10, 1992, Pat. No. 5,367,065.

[51] Int. Cl.$^6$ .................................................. A01H 4/00
[52] U.S. Cl. ............................ 800/205; 800/DIG. 15; 435/419; 435/410
[58] Field of Search ............................... 536/23.2, 23.6; 435/240.4; 800/205, DIG. 15

[56] References Cited

PUBLICATIONS

Harpham et al. The effect of Ethylene on the Growth and Development of Wild–type and Mutant Arbaidopsis Tahliana *Heynh Annals of Botany* 1991 68:55.
Boller T. The Plant Hormone Ethylene A. K. Mattoo and J. C. Suttle eds. CRC Press, Inc. Boca Raton 1991 293–314.
Yu et al. Regulation of Auxin–induced Ethylene Production in *1979 Mung Bean Hypocotyls Plant Physiol.* 63:589–590.
Guzman and Ecker, Exploiting the Triple Response of Arabidopsis to Identify Ethylene–Related Mutants *The Plant Cell* 1990 2:513–523.
Sato and Theologis Cloning the mRNA encoding 1–aminocyclopropan–1–carboxylate syntase the key enzyme for ethylene biosynthesis in plants *Proc. National Acad. Sci* 1989 86:6621–6625.
Van Der Straeten et al. Cloning and sequence of two different cDNAs encoding 1–aminocyclopropane–1–carboxylate synthase in tomato *Proc. National Sci* 1990 87:4859–4863.
Nakajima et al. Molecular Cloning and Sequence of a Complementary DNA Encoding 1–Aminocyclopropane–1–carboxylate Synthase Induced by *Tissue Wounding Plant Cell Physiol.* 1990 31(7):1021–1029.
Spanu et al. Analysis and Cloning of the Ethylene–forming enzyme from tomato by functional expression of its mRNA in Xenopus Laevis oocytes *The EMBO Journal* 1991 10:2007–2103.

Blinder et al., Constitutive Mutatns in the Yeast Pheromone Response: Ordered Function of the Gene Products Cell 1989 56:479–486.
Nakajima et al., Molecular Cloning and Sequence of a Complementary DNA Encoding 1–Aminocyloporpane–1–carboxylate Synthase Induced by Tissue Wounding Plant Cell Physiol. 29:989 1990.
Kende, Enzymes of Ethylene Biolsynthesis Plant Physiol., 1989 91:1–4.
Theologis, A., One Rotten Apple Spoils the Whole Bushel: The Role of Ethylene in Fruit Ripening Cell 70:181 1992.
Yang et al., Ehtylene Biosynthesis and its Regulation in Higher Plants Ann. Rev. Plant Physiol. 1984 35:155.
McGarvey et al., Ripening–Related Gene from Avocado Fruit Plant Physiol. 1992 98:554.
Neljubow, D., Pflanzen Beih. Bot. Zentralb. 10: 128 1901.
Sambrook et al., Molecular Cloning: A Laboratory Manual, 2nd ed., Cold Spring Harbor Laboratory Press, Cold Spring Harbor, NY 1989.
Feldman et al., Agrobacterium–mediated transformation of germinating seeds of Arabidopsis thaliana: A non–tissue culture approach *Mol. Gen. Genet.* 208:1 1987.
Feldman, K. A., *Plant Journal* 1:71 1991.
Beyer, Jr., E. M., A Potent Inhibitor of Ethylene Action in Plants Plant Physiol 1976 58:268.
Sisler et al., *Plant Growth Reg.* 1990 9:157.
Matallana et al., *Methods in Arabidopsis Research*, Koncz et al., Eds Singapore: World Scientific, pp. 144–169.
Jefferson et al., GUS fusions:β–1glucuronidase as a sensitive and versatile gene fusion marker in higher plants *EMBO Journal* 1987 6:3901–3907.
Valvekens, Agrobacterium tumefaciens–mediated transformation of Arabidopsis thaliana root explants by using kanamycin selection PNAS 1988 85:5536–5540.
Abeles et al., Ethylene in Plant Biology Second Edition 1992.

*Primary Examiner*—Che S. Chereskin
*Attorney, Agent, or Firm*—Woodcock Washburn Kurtz Maciewicz & Norris

[57] ABSTRACT

The present invention is directed to nucleic acid sequences for constitutive triple response mutants and corresponding amino acid sequences. Several ctr mutations are included within the scope of the present invention. The nucleic acid sequences set forth in SEQUENCE ID NUMBERS 1, and 3–6 as well as amino acid sequences set forth in SEQUENCE ID NUMBERS 1 and 2 are particular embodiments of the present invention.

15 Claims, 7 Drawing Sheets

1 2 3 4 5 wt eto1 ctr1

Wild-type    ctr1

Wild Type | Wild Type + Ethylene | ctr1

5,602,322

1

CONSTITUTITIVE TRIPLE RESPONSE GENE AND MUTATIONS

REFERENCE TO GOVERNMENT GRANTS

This work was supported in part by research grants from the National Science Foundation, grant number DCB-9008323 and National Institutes of Health, grant numbers GM38894 and GM42471. The United States Government may have certain rights in this invention.

This application is a continuation-in-part of U.S. patent application Ser. No. 003,311, filed Jan. 12, 1993, now U.S. Pat. No. 5,444,166, which is a continuation-in-part of U.S. patent application Ser. No. 928,464, filed Aug. 10, 1992, now U.S. Pat. No. 5,367,065, the disclosures of which are hereby incorporated by reference in their entirety.

BACKGROUND OF THE INVENTION

Ethylene is one of five well-established plant hormones. It mediates a diverse array of plant responses including fruit ripening, leaf abscission and flower senescence.

The pathway for ethylene biosynthesis has been established (FIG. 1). Methionine is converted to ethylene with S-adenylmethionine (SAM) and 1-aminocyclopropane-1-carboxylic acid (ACC) as intermediates. The production of ACC from SAM is catalyzed by the enzyme ACC synthase. Physiological analysis has suggested that this is the key regulatory step in the pathway, (Kende, *Plant Physiol.*, 91:1–4 (1989). This enzyme has been cloned from several sources (Sato et al., *PNAS, (USA)* 86:6621 (1989); Van Der Straeten et al., *PNAS, (USA)* 87:4859–4863 (1990); Nakajima et al., *Plant Cell Physiol.* 29:989 (1990.). The conversion of ACC to ethylene is catalyzed by ethylene forming enzyme (EFE), which has been recently cloned (Spanu et al., *EMBO J* 10:2007 (1991). Aminoethoxy-vinylglycine (AVG) and α-aminoisobutyric acid (AIB) have been shown to inhibit ACC synthase and EFE respectively. Ethylene binding is inhibited non-competitively by silver, and competitively by several compounds, the most effective of which is trans-cyclooctane. ACC synthase is encoded by a highly divergent gene family in tomato and Arabidopsis (Theologis, A., *Cell* 70:181 (1992)). ACC oxidase, which converts ACC to ethylene, is expressed constitutively in most tissues (Yang et al., *Ann. Rev. Plant Physiol.* 35:155 (1984)), but is induced during fruit ripening (Gray, 1992). It has been shown to be a dioxygenase belonging to the Fe2+/ascorbate oxidase superfamily (McGarvey et al., *Plant Physiol.* 98:554 (1992)).

Etiolated dicotyledonous seedlings are normally highly elongated and display an apical arch-shaped structure at the terminal part of the shoot axis; the apical hook. The effect of ethylene on dark grown seedlings, the triple response, was first described in peas by Neljubow in 1901, Neljubow, D., *Pflanzen Beih. Bot. Zentralb.* 10: 128 (1901). In Arabidopsis, a typical triple response consists of a shortening and radial swelling of the hypocotyl, an inhibition of root elongation and an exaggeration of the curvature of the apical hook (FIG. 2A). Etiolated morphology is dramatically altered by stress conditions which induce ethylene production the ethylene-induced "triple response" may provide the seedling with additional strength required for penetration of compact soils, see Harpham et al., *Annals of Bot.* 68:55 (1991). Ethylene may also be important for other stress responses. ACC synthase gene expression and ethylene production is induced by many types of biological and physical stress, such as wounding and pathogen infection, see Boller, T., in *The Plant Hormone Ethylene*, A. K. Mattoo and J. C. Suttle eds., 293–314 (1991), CRC Press, Inc. Boca Raton and Yu, Y. et al., *Plant Phys.* 63:589 (1979).

A collection of mutants affected in this response has been isolated. One class, the ein mutants (ethylene insensitive), are completely insensitive to ethylene. A second class of mutants are affected in only subset of the seeding responses. The hls1 mutant (hookless) completely lacks an apical hook either in the presence or absence of ethylene.

Constitutive hormone response mutants have been useful in elucidating mechanisms that underlie other hormone-mediated responses (e.g. yeast mating factor, Blinder et al., *Cell* 56:479 (1989)). Despite the information known about ethylene biosynthesis, how plants perceive and transduce hormone signals is almost completely unknown. While many of the components found in animal signal transduction chains have been found in plants, including kinases, and G proteins, no definitive correlation of these signal transducers with any hormone signal has been established. Elucidation of the complex role of these signal molecules would be greatly aided by the isolation of gene mutations which are affected in different steps in the signal transduction pathway.

The present invention addresses these important needs. A novel *Arabidopsis thaliana* mutant has been identified that constitutively exhibits seedling and adult ethylene responses in the absence of the hormone. The constitutive triple response (ctr) mutants display the "ethylene" phenotypes even in the presence of inhibitors of ethylene biosynthesis or receptor binding. ctr1 has a dramatically altered adult morphology that can be phenocopied in wild-type plants by growth in 1 ppm ethylene. Seedling and adult ctr1 plants show high-level constitutive expression of mRNAs for several ethylene inducible genes. Genetic, molecular and biochemical characterization of the CTR1 gene and protein product is set forth in the present invention. Genetic characterization of the interactions among modulatory components of the ethylene action pathway will provide insight into how plant hormones function. Thus, the quality, quantity and longevity of food, such as fruits and vegetables, and other plant products such as flowers, will be improved for market in both developed and undeveloped countries.

SUMMARY OF THE INVENTION

The present invention is directed to nucleic acid sequences for constitutive triple response, ctr, gene and corresponding amino acid sequence. Several ctr mutations, amino acid sequences and the corresponding protein products are included within the scope of the present invention. The nucleic acid sequences set forth in SEQUENCE ID NUMBERS 1, and 3–7 as well as amino acid sequences set forth in SEQUENCE ID NUMBERS 1 and 2 are particular embodiments of the present invention.

BRIEF DESCRIPTION OF THE FIGURES

FIGS. 5A–B display the effects of ethylene on leaf morphology and cell size. FIG. 5A shows a comparison of mutant and wild-type plants grown in air and 1 μl of $C_2H_4$/liter of air. Plants were grown as described. Representative individuals were picked and photographed. FIGS. 5B–D shows Nomarski microscopy of leaf epidermal cells. Individual leaves were excised from plants grown as described, fixed as described, and photographed under Nomarski optics. The leaf veins are visible as long streaks of light in FIGS. 5C and 5D and the tip of a trichome is seen in top right of FIG. 5C. The doughnut-shaped stomata are also clearly visible.

FIG. 6A is a Northern blot of RNA isolated from three day-old etiolated wild-type (lanes 1 and 2) or mutant (lanes 3 and 4) seedlings grown in air (lanes 1 and 3) or 10 μl $C_2H_4$/liter of air (lanes 2 and 4). Twenty μg of total RNA was loaded in each lane and northern blots performed as described. The blot was probed pEI305, stripped and hybridized with an rDNA probe as a control for loading. FIG. 6B is a Northern blot of RNA isolated from 18 day-old wild-type (lanes 1 and 2) and ctr1 (lanes 2 and 4) adult plants grown under continuous light and then shifted for 48 hours to a chamber through which air (lanes 1 and 3) or 10 μl $C_2H_4$/liter of air (lanes 2 and 4) was passed. The gel was run and hybridized as above except 40 μg of total RNA was loaded and parallel blots were run rather than stripping one blot. One blot was hybridized with a chitinase probe and the second with an rDNA probe.

FIG. 7A is a Southern blot of genomic DNA. Five μg of genomic DNA from wild-type (lanes 1, 3, and 5) and the T-DNA insertional line ctr1-5 (lanes 2, 4, and 6) was digested with EcoRI (lanes 1 and 2), BamHI (lanes 3 and 4) or PvuII (lanes 5 and 6), electrophoresed through a 0.8% agarose gel, and blotted to a nylon membrane. The blot was hybridized as described with the insert from pCTG1, which contained the E. coli-rescued plant DNA from ctr1-5.

FIG. 7B is a northern blot of poly(A+) RNA. RNA was isolated from air-grown, adult wild-type (lane 1) or ctr1-5 (lane 2) and wild-type seedlings grown in air (lane 3) or 10 μl $C_2H_4$/liter of air (lane 4). Twenty μg of RNA was electrophoresed through a 1% agarose gel and blotted onto nylon membrane. The blot was hybridized to a cDNA insert containing the entire CTR1 coding region as described. The probe was then removed and the blot hybridized with DNA containing the entire coding region from the Arabidopsis topoisomerase I gene (TOP) (Kieber et al., 1992) to control for loading differences. Using size standards (Bethesda Research Laboratories), the CTR1 transcript was determined to be approximately 3.2 kb in size.

DETAILED DESCRIPTION OF THE INVENTION

Figure 1:
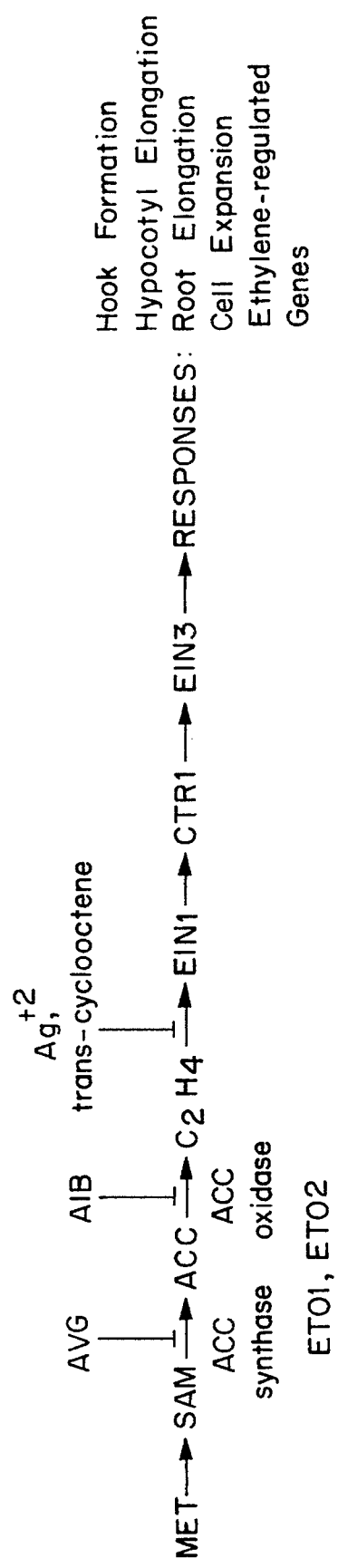
FIG. 1 is a schematic illustration of the ethylene biosynthetic pathway.

The present invention is directed to constitutive triple response, ctr, nucleic acid sequences and corresponding amino acid sequences. In accordance with the present invention, the CTR gene is identified. Several ctr mutations are included within the scope of the present invention. The nucleic acid sequences set forth in SEQUENCE ID NUMBERS 1, and 3–7 as well as amino acid sequences set forth in SEQUENCE ID NUMBERS 1 and 2 are particular embodiments of the present invention.

Specifically, SEQUENCE ID NO: 1, the isolated cDNA representing the nucleic acid sequence coding for CTR and the isolated genomic CTR DNA sequence of SEQUENCE ID NO: 3 are particularly preferred embodiments of the invention. The purified amino acid sequence of SEQUENCE ID NUMBERS 1 and 2 represent the CTR protein product encoded by the cDNA identified above. The ctr1-2 mutation set forth in SEQUENCE ID NO: 4 has a 17 base pair deletion, beginning at nucleotide position 1995 of CTR genomic DNA sequence of FIG. 8, corresponding to the position 2770 in SEQUENCE ID NO: 3. The ctr1-2 mutation of SEQUENCE ID NO: 4 was generated by x-ray mutagenesis. The ctr1-3 mutation set forth in SEQUENCE ID NO: 5 has a "C" to "T" point mutation resulting in a stop codon at position 1927 of CTR genomic DNA sequence of FIG. 8, corresponding to the position 2702 in SEQUENCE ID NO: 3. The ctr1-3 mutation of SEQUENCE ID NO: 5 was generated by EMS mutagenesis. In the resulting protein product, "arg" is converted to a stop signal. The ctr1-1 mutation set forth in SEQUENCE ID NO: 6 has a "T" to "A" point mutation at nucleotide position 3295 of CTR genomic DNA sequence of FIG. 8, corresponding to the position 4800 in SEQUENCE ID NO: 3. The ctr1-1 mutation of SEQUENCE ID NO: 6 was generated by DEB mutagenesis. Another mutation, ctr1-4, see SEQUENCE ID NO: 7, was generated by EMS mutagenesis and has a "G" to "A" transition at position 3233 of FIG. 8, corresponding to the position 4008 of SEQ ID NO: 3 that is predicted to result in a "Glu" to "Lys" change at amino acid 596, another invariant residue in all kinase catalytic domains. ctr1-5 comprises a T-DNA insertion at position 3041 in intron 7 of CTR genomic DNA sequence wherein 25 base pairs were deleted from the left border of the T-DNA at the junction with plant DNA.

In accordance with the present invention, nucleic acid sequences include and are not limited to DNA, including and not limited to cDNA and genomic DNA; RNA, including and not limited to mRNA and tRNA; and suitable nucleic acid sequences such as those set forth in SEQUENCE ID NOS: 1, and 3–6, and alterations in the nucleic acid sequences including alterations, deletions, mutations and homologs.

Also amino acid, peptide and protein sequences within the scope of the present invention include, and are not limited to the sequence set forth in SEQUENCE ID NO: 2, the amino acid sequences corresponding to nucleic acids in SEQUENCE ID NOS: 1 and 3–6, and alterations in the amino acid sequences including alterations, deletions, mutations and homologs.

In accordance with the invention, the CTR and ctr nucleic acid sequences employed in the invention may be exogenous sequences. Exogenous or heterologous, as used herein, denotes a nucleic acid sequence which is not obtained from and would not normally form a part of the genetic makeup of the plant or the cell to be transformed, in its untransformed state. Plants comprising exogenous nucleic acid sequences of CTR or ctr mutations, such as and not limited to the nucleic acid sequences of SEQUENCE ID NUMBERS: 1 and 3–6 are within the scope of the invention.

Transformed plant cells comprising nucleic acid sequences of CTR or ctr mutations, such as and not limited to the nucleic acid sequences of SEQUENCE ID NUMBERS: 1 and 3–6, are within the scope of the invention. Transformed cells of the invention may be prepared by employing standard transformation techniques and procedures as set forth in Sambrook et al., *Molecular Cloning: A Laboratory Manual*, 2nd ed., Cold Spring Harbor Laboratory Press, Cold Spring Harbor, N.Y. (1989).

The action of the plant hormone ethylene utilizing the "triple response" of *Arabidopsis thaliana* was studied. The "triple response" in Arabidopsis consists of three distinct morphological changes in dark-grown seedlings upon exposure to ethylene: inhibition of hypocotyl and root elongation, radial swelling of the stem and exaggeration of the apical hook. A class of constitutive mutants, ctr, display a constitutive triple response in the presence of ethylene biosynthetic inhibitors, and is most likely affected at, or downstream of the receptor. Based on the results of genetic experiments, over-expression of the normal or truncated versions of the negative regulatory gene CTR1 in transgenic plants would be predicted to result in a dominant ethylene-insensitive phenotype.

Several ctr alleles have been identified, ctr1-1 to ctr1-5. ctr1 mutants are recessive, do not produce elevated levels of ethylene and have a dramatically altered seedling and adult morphology. The adult phenotype of ctr1 can be phenocopied by growth of wild-type plants in the presence of 1 ppm ethylene and is shown to result, at least in part, to a reduction in cell size.

The present invention is directed to a method of inducing a constitutive triple response in wild-type plants by growing the wild-type plants in the presence of from about 1 ppm to about 10 ppm ethylene for about 2 weeks to about 3 weeks.

At the molecular, cellular and whole plant level, and in seedling and adult plants, air-grown ctr1 mutants strongly resemble ethylene-treated wild-type plants. The recessive nature of ctr suggests that the ethylene-response pathway is normally under negative regulation and loss of function of the CTR repressing activity results in a constitutive triple response phenotype.

The gene corresponding to CTR has been cloned as set forth below and the sequence of cDNA clone is described. The gene encodes a protein that resembles the Raf family of serine/threonine kinases. Physiological, biochemical and genetic evidence indicates that the CTR1 and EIN3 gene products are required for transduction of the ethylene signal in both etiolated seedling and adult plants. The putative CTR1 kinase is postulated to act as a negative regulator in the ethylene signal transduction chain.

Also disclosed herein is a recessive mutation referred to as ein3 which causes insensitivity to ethylene whereas ctr1 results in constitutive activation of all known ethylene responses in the absence of ethylene. EIN3 may act as a positive regulator whereas CTR1 gene product appears to act as a negative regulator in the ethylene action pathway. The predicted protein sequence of EIN3 and EIL1, an EIN3 related gene, are reminiscent of transcription factors. These include acidic and basic domains and mono-amino acid repeat motifs. The EIN3 and EIL1 proteins may be targets for phosphorylation by the CTR1 kinase. Double mutant analysis indicated that the EIN3 gene product acts downstream of the CTR1 gene product in the ethylene signal transduction pathway. CTR1, in turn, acts downstream of EIN2 and EIN1/ETR1.

In accordance with the present invention, the present plants included within the scope of the present invention are higher and lower plants of the Plant Kingdom. Mature plants and seedlings are included in the scope of the invention. A mature plant includes a plant at any stage in development beyond the seedling. A seedling is a very young, immature plant in the early stages of development.

Transgenic plants are included within the scope of the present invention which have a phenotype characterized by the CTR gene or ctr mutations. Particularly preferred plants are those from: the Family Umbelliferae, particularly of the genera Daucus (particularly the species *carota*, carrot) and Apium (particularly the species *graveolens dulce*, celery) and the like; the Family Solanacea, particularly of the genus Lycopersicon, particularly the species *esculentum* (tomato) and the genus Solanum, particularly the species *tuberosum* (potato) and *melongena* (eggplant), and the like, and the genus Capsicum, particularly the species *annum* (pepper) and the like; and the Family Leguminosae, particularly the genus Glycine, particularly the species *max* (soybean) and the like; and the Family Cruciferae, particularly of the genus Brassica, particularly the species *campestris* (turnip), *oleracea* cv Tastie (cabbage), *oleracea* cv Snowball Y (cauliflower) and *oleracea* cv Emperor (broccoli) and the like; the Family Compositae, particularly the genus Lactuca, and the species *satira* (lettuce), and the genus Arabidopsis, particularly the species *thaliana* (Thale cress) and the like. Of these Families, the most preferred are the leafy vegetables, for example, the Family Cruciferae, especially the genus Arabidopsis, most especially the species *thaliana*.

The present invention will benefit plants in relation to stress. Stress includes, and is not limited to, infection as a result of pathogens such as bacteria, viruses, fungi; wound healing and soil penetration. Bacterial infections include, and are not limited to, *Clavibacter michiganense* (formerly *Coynebacterium michiganense*), *Pseudomonas solanacearum* and *Erwinia stewartii*, and more particularly, *Xanthomonas campestris* (specifically pathovars *campestris* and *vesicatoria*), *Pseudomonas syringae* (specifically pathovars *tomato*, *maculicola*).

In addition to bacterial infections, other examples plant viral and fungal pathogens within the scope of the invention include and are not limited to, tobacco mosaic virus, cauliflower mosaic virus, turnip crinkle virus, turnip yellow mosaic virus; fungi including *Phytophthora infestans*, *Peronospora parasitica*, *Rhizoctonia solani*, *Botrytis cinerea*, *Phoma lingam* (*Leptosphaeria maculans*), and *Albugo candida*.

The present invention is further described in the following examples. These examples are not to be construed as limiting the scope of the appended claims.

EXAMPLE 1

Isolation of Constitutive Mutants

Independent lots of ethyl methanesulfonate (EMS), diepoxybutane (DEB) and X-ray mutagenized seeds were screened for mutants that constitutively display the triple response by plating on agar in the absence of added ethylene in the dark, see Table 1. A total of greater than $10^6$ seedlings were screened in this manner, yielding 400 putative mutants, of which 18 mutants survived and produced seeds. These 18 were retested for this phenotype.

*Arabidopsis thaliana* ecotype Columbia was the parent strain for mutant isolation, with the exception of the T-DNA tagged allele which was isolated from a population developed by Feldman and Marks in the Wassilewskija ecotype. Feldman et al., *Mol. Gen. Genet.* 208:1 (1987) and Feldman, K. A., *Plant Journal* 1:71 (1991). Marker lines were obtained from the Arabidopsis Biological Resource Center, Ohio State University, and were as follows: W11 lu tt3; W13 ttg yi; NW85 tt4. Triple response screens were performed on petri plates as described by Guzman et al., *The Plant Cell* 2:513 (1990). The following concentrations of inhibitors were used: AVG (10 μM), $AgNO_3$ (17 μg/ml), AIB (2 mM) and trans-cyclooctene (90 μl gas/liter of air). EMS mutagenized seeds were obtained as described by Guzman et al., supra. For X-ray mutagenesis, hydrated seeds were treated with 20,000 rads (30 cm from the source for 43 minutes using a 2mA1 filter at the Hospital of the University of Pennsylvania) and then grown as 20 independent lots; 1,500 plants per 35 cm×45 cm tub. For the diepoxybutane, DEB, mutagenesis, seeds were soaked in water overnight, then soaked in 22 mM DEB for 4 hours, washed extensively and grown in 20 independent lots as above. Plants were generally grown in METRO-MIX™ 200 (Grace) in continuous illumination with fluorescent light at 25° C. and watered with a 15-16-17 (Nitrogen-phosphorous-potassium) nutrient solution, also known as Peter's lite, every fourth watering.

For growth of adult plants in ethylene, seeds were sown in 6" pots in METRO-MIX™ and placed in the growth room in chambers sealed with tape. Hydrocarbon-free air or 1 μl $C_2H_4$/liter of air was continuously passed through the chamber at a flow rate of approximately 40 ml/min.

Figure 2A:
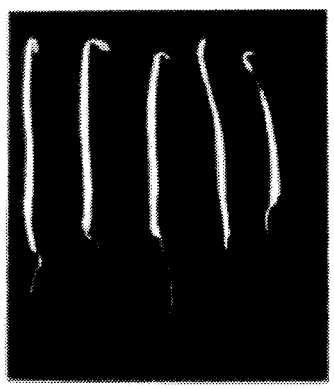
FIG. 2A exhibits the phenotypes of Arabidopsis seedlings. Surface-sterilized seeds were plated on growth medium and cold treated for four days (4° C.) before germination and growth in the dark at 23° C. for 72 hours. The wild-type (FIG. 2A), ctr1 (FIG. 2C), and eto1 (FIG. 2B) controls seedlings were grown in 1) no inhibitor, 2) AVG, 3) AIB, 4) AgNO$_3$ and 5) trans-cyclooctene. Representative seedlings are shown, except the AVG-treated wild-type seedling in which the root was broken prior to photography.
Figure 2B:
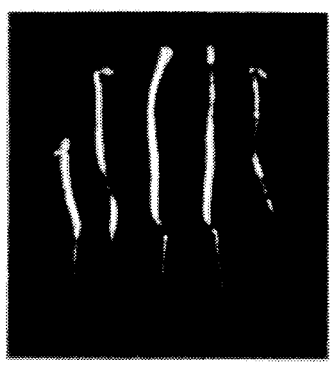
FIG. 2D exhibits phenotypes of wild-type and ctr1 adult plants. Seeds were sown in soil and grown under continuous light at 22°–27° C. in individual pots for 18 days.

Several inhibitors of ethylene biosynthesis and binding have been described (FIG. 1), and these were examined for their ability to revert the constitutive phenotype of these mutants. Aminoethoxyvinylglycine (AVG), an effective inhibitor of pyridoxal phosphate-mediated enzyme reactions, inhibits ACC synthase, the penultimate step in ethylene biosynthesis which converts S-adenyl-methionine (SAM) to 1-aminocyclopropane-l-carboxylic acid (ACC). α-aminoisobutyric acid (AIB), a structural analog of ACC, has been shown to competitively inhibit the formation of ethylene from ACC, and thus block ACC oxidase. Satoh et al., *Physiol. Plant.* 5:521 (1983) and Yang et al., supra. Trans-cyclooctene has been shown to be an extremely effective competitive inhibitor of ethylene binding, and silver ion has been shown to be a potent non-competitively inhibitor of ethylene action in several classic ethylene responses. Beyer, Jr., E. M., *Plant Physiol* 58:268 (1976) and Sisler et al., *Plant Growth Reg.* 9:157 (1990). The mutants fell into two classes, those in which the constitutive triple response phenotype was efficiently reverted by all four inhibitors, class 1 (FIG. 2A) and those that were completely unaffected by all four compounds, class 2 (FIG. 2A). This strongly suggested that the constitutive triple response phenotype of the first class was due to an over-production of ethylene, whereas the second class was affected in the perception of ethylene. Measurements of ethylene production confirmed that all the class 1 mutant seedlings, which included the previously identified eto1 mutation, did overproduce ethylene.

All of the recessive Eto mutants failed to complement eto1-1. Three additional dominant Eto mutations were identified. The eto2 mutation was completely dominant (Table 1), produced twenty-fold more ethylene than wild-type seedlings and mapped to the bottom of chromosome 5, close to the yi mutation (2.2±0.8 cM). The eto3 mutation was also completely dominant, produced 100-fold more ethylene than wild-type seedlings and may be allelic to eto2. All Eto adult plants produced thee same or only slightly more ethylene than wild-type adults, which suggests that perhaps the production of ethylene is regulated by independent pathways in seedling and adult plants or in light and dark grown plants. Alternatively, a negative feedback mechanism may repress excess ethylene production in adult Eto mutants.

Figure 3:
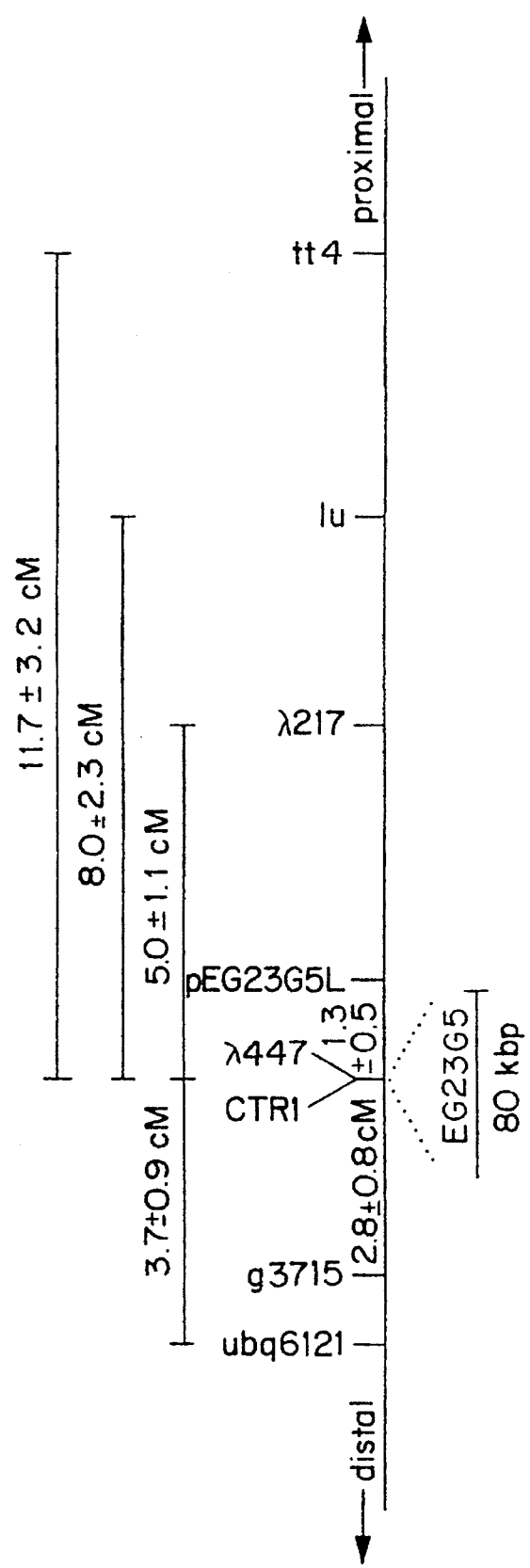
FIG. 3 displays the genomic region corresponding to the top of chromosome 5, with proximal and distal referring to the orientation on the chromosome. The genetic distance (in cM) between two mapped markers is indicated above the given interval, plus or minus the standard error. The morphological markers lu and tt4 were mapped relative to the ctr1 mutation. Shown below the map is the position of pEG23GSL, a left end rescue from the YAC EG23G5 (Grill and Somerville, 1991). CTR1 and λ447 are contained within this YAC and several other clones (not shown) as indicated by the dotted lines. A recombinant inbred (RI) population was used to map RFLPs detected by CTR1, pEG23G5L, g3715, λ271 and ubq6121.
Figures 4A, 4B, 4C, 4D, 4E:
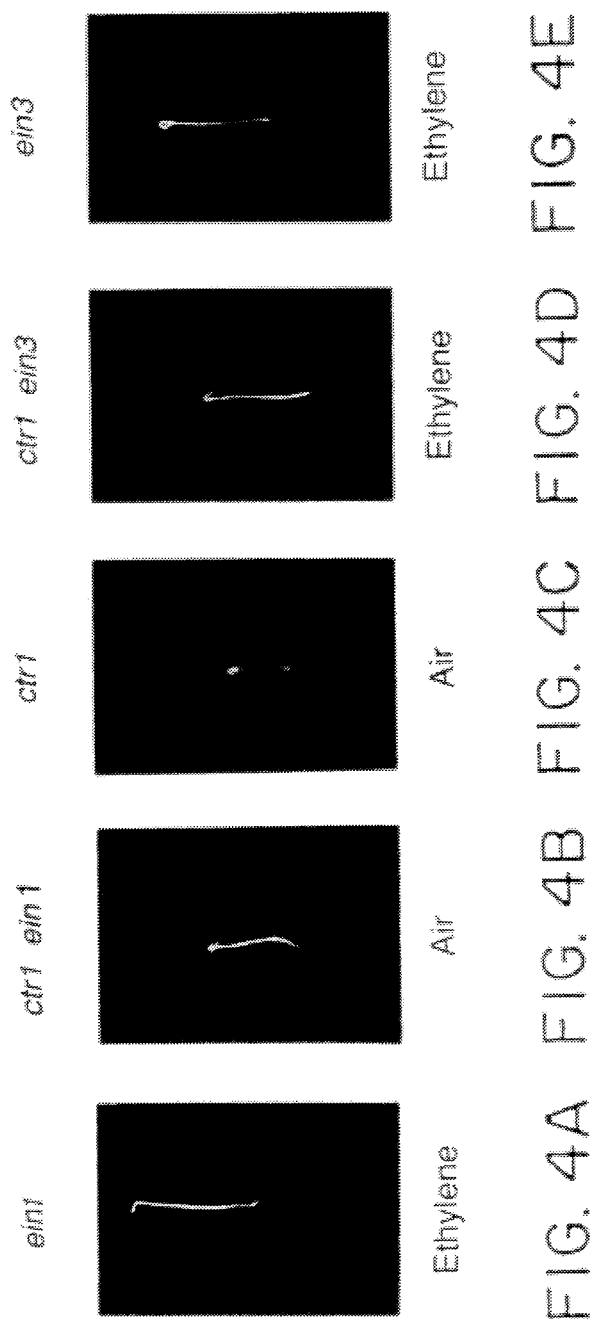
FIGS. 4A–E display the double mutants constructed as described below. Seeds of wild-type and the mutants were plated and placed in the dark in chambers with air or in the presence of 10 μl $C_2H_4$/liter of air as indicated. After 72 hours representative seedlings were picked and photographed.
Figure 5A:
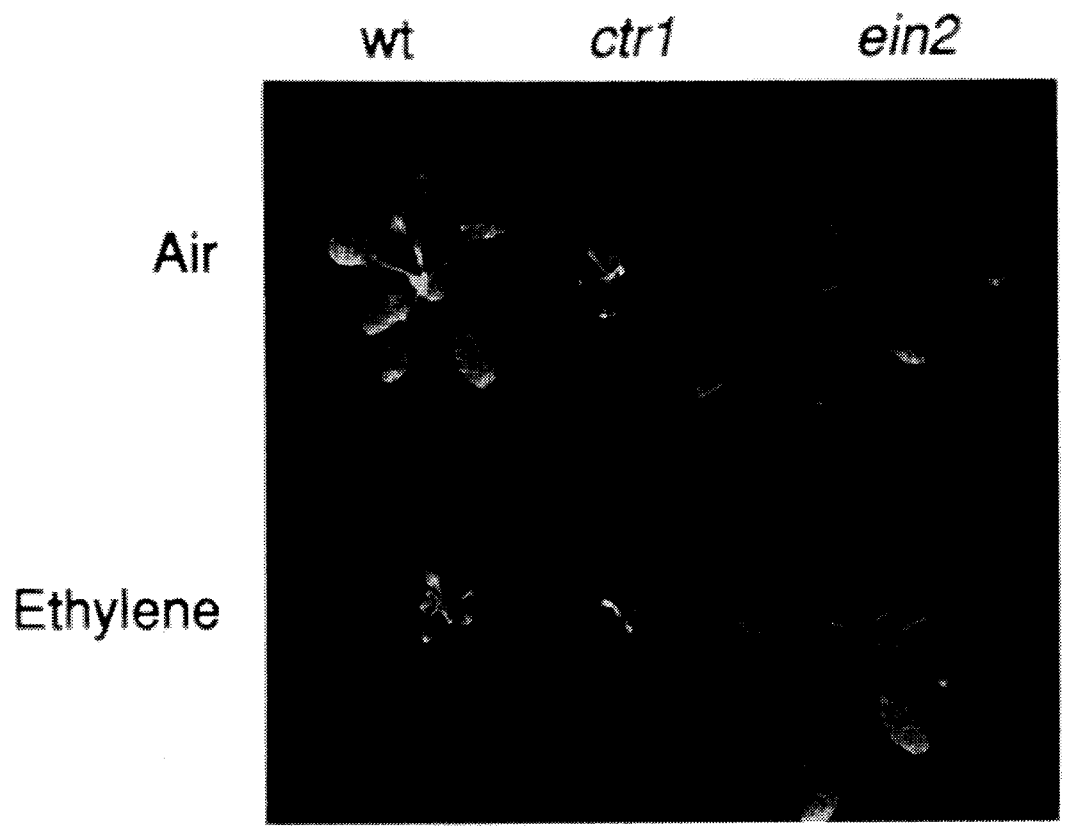
Figures 5B, 5C, 5D:
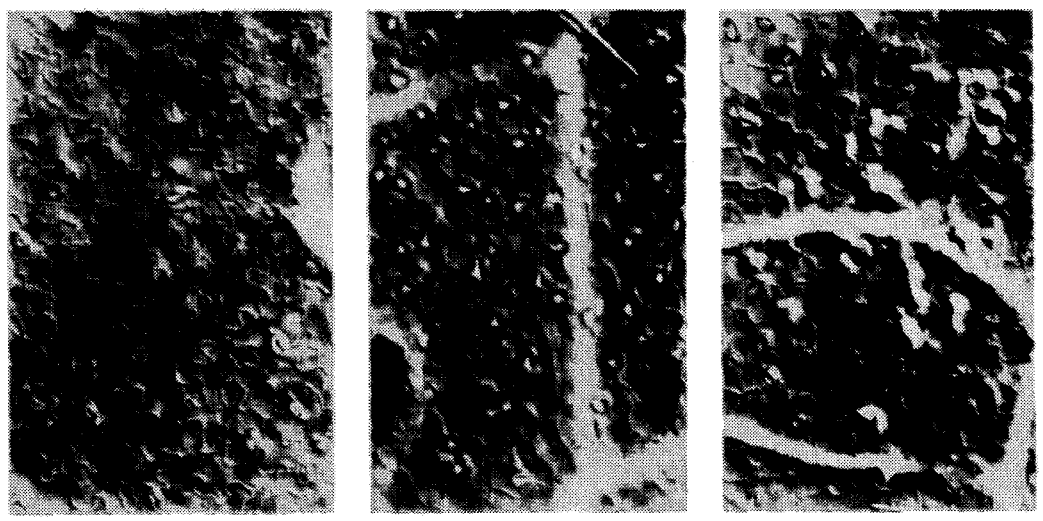

All of the class 2 mutants fell into one complementation group, ctr1. Neither ctr1 seedlings nor adult plants produced significantly more ethylene than wild-type plants. The ctr1 mutation is recessive and segregates in a manner most consistent with a single Mendelian gene, although it differs significantly from the expected 3:1 ratio as judged by chi-square analysis (Table 1). The altered segregation ratio (4.8 wild-type: 1 ctr1) is most likely due to a decrease in transmission of the ctr1 allele relative to wild-type, which may result from such factors as a decrease in gametophyte viability or pollen tube growth rate. The mutation was mapped using visible markers to the top of chromosome 5, close to tt4 and lu mutations (FIG. 3). Using restriction fragment length polymorphism (RFLP) markers, close linkage was detected with the RFLPs λ447 and ubq6121 on chromosome 5 (FIG. 3). No recombinants were observed between λ447 and the ctr1 mutation (out of 86 chromosomes) in an F2 mapping population generated from a cross of ctr1 (ecotype Columbia) to a wild-type plant of the Niederzenz ecotype.

EXAMPLE 2

Genetic Analysis of Mutants

Crosses were performed as described Guzman and Ecker, supra. RFLP analysis was performed by crossing ctr1-1 (Columbia background) to a wild-type plant of the Niederzenz ecotype. Individual F3 families were grown and DNA isolated by CsCl banding. The restriction patterns of DNA hybridizing to the RFLP probes from each of the F3 families was analyzed by Southern blotting. DNA probes were prepared by random hexamer labeling.

The cloned CTR1 gene was mapped relative to the RFLP markers ubq6121, λ217 and g3715 using recombinant inbred lines (kindly provided by Caroline Dean, John Innes Institute, Norwich, U.K.) and distances calculated using RI plant Manager program v2.2 developed by Kenneth Manly (Buffalo, N.Y.). YACs were screened with CTR1 and λ447 and the ends rescued as described in Matallana et al., *Methods in Arabidopsis Research*, Koncz et al., Eds., Singapore: World Scientific, pgs 144–169 (1992).

TABLE 1

| Genetic Analysis of Constitutive Triple Response Mutants | | | | | |
|---|---|---|---|---|---|
| | | | Constitutive Triple Res.[b] | | |
| Cross[a] | Type | Total | + | − | $X^{2c}$ |
| ctr1-1/ctr1-1 X CTR1/CTR1 (DEB)[d] | F1 F2 | 75 1924 | 0 333 (4.8:1) | 75 1591 | 60.7 $p < .05$ |
| ctr1-2/ctr1-2 X CTR1/CTR1 (X-ray) | F1 F2 | 62 264 | 0 45 (4.9:1) | 62 219 | 9.8 $p < .05$ |
| ctr1-1/ctr1-1 X | F1 | 13 | 13 | 0 | |

TABLE 1-continued

Genetic Analysis of Constitutive Triple Response Mutants

| Cross[a] | Type | Total | Constitutive Triple Res.[b] + | − | $X^{2c}$ |
|---|---|---|---|---|---|
| ctrl-2/ctrl-2 (X-ray) ctrl-1/ctrl-1 X ctrl-3/ctrl-3 (EMS) | F1 | 16 | 16 | 0 | |
| ctrl-1/ctrl-1 X ctrl-4/ctrl-4 (EMS) | F1 | 11 | 11 | 0 | |
| ctrl-1/ctrl-1 X ctrl-5/ctrl-5 (T-DNA) | F1 | 28 | 28 | 0 | |
| ETO2/ETO2 X eto2/eto2 (DEB) | F1 F2 | 17 578 | 17 422 | 0 156 | 1.2 $p > 0.1$ |
| ETO3/ETO3 X eto3/eto3 (DEB) | F1 | 36 | 36 | 0 | |

[a]Crosses were preformed as described in Experimental Procedures.
[b]Seedlings were scored for the triple response in the absence of ethylene as described in Experimental Procedures.
[c]Chi-square was calculated for an expected 3:1 ratio.
[d]Parenthesis indicate mutagen used to generate allele.

The epistatic relationships between ctrl and several mutations that result in insensitivity to ethylene (EIN) was examined. ein1 is a single gene, dominant mutation that results in insensitivity to ethylene in both seedlings and adult plants. ein3 is a second, recessive mutation that has a somewhat weaker ethylene-insensitive phenotype. Crosses were carried out between ctrl, ein1 and ein3. The double mutants were identified and their seedling (FIGS. 4A–E) and adult phenotypes examined.

Double mutants were constructed by crossing the two parents and collecting seeds from individual F1 plants. The F2 seeds were plated in air and ethylene in the dark, Guzman et al., supra and seedlings corresponding to each parental phenotype were picked and grown. These F2 individuals were progeny-tested by collecting and then plating their seeds in air and ethylene. Putative double mutants were grown and their genotype tested by crossing to wild-type to examine for segregation of the two parental phenotypes.

The double mutants were identified and their seedling and adult phenotypes examined. The ctrl ein1 double mutant displayed the constitutive ethylene phenotypes, see FIGS. 4A–E, whereas the ctrl ein3 double mutant showed an ethylene-insensitive phenotype. These results suggest that the CTR1 gene product acts at, or downstream of the ein1 gene product, and at or upstream of the EIN3 gene product in the ethylene signal transduction chain, FIG. 1.

EXAMPLE 3

Ethylene-Induced Genes are Constitutively on in the ctrl Mutant

The steady state level of several ethylene-induced transcripts was examined in both seedlings and mature ctrl plants. EI305 is a random transcript that was isolated by differential screening of ethylene and air treated seedlings. The basic chitinase gene and β 1,3 glucanase genes have been shown to be induced by ethylene in adult plants.

Seeds were sterilized and one mg per plate (150 mm) was plated. Seedlings were grown in the dark with either hydrocarbon free air or 10 μl $C_2H_4$/l of air blowing through at approximately 60 ml/minute for 48 hours. Seedlings were harvested by pouring liquid nitrogen on the plate and then scraping the frozen seedlings into liquid nitrogen. Adult plants were grown in growth chambers until just beginning to bolt, and moved to chambers through which air or 10 μl $C_2H_4$/liter of air was blowing at approximately 60 ml/minute for 48 hours. The aerial portions of the plants were harvested into liquid nitrogen and stored at −70° C. until use. Total RNA was prepared by extraction with phenol/chloroform, polyA RNA isolated by oligoT-cellulose affinity columns and Northern analysis was as described by Sambrook, et al., *Molecular Cloning: A Laboratory Manual*, 2nd ed., Cold Spring Harbor Laboratory Press, Cold Spring Harbor, N.Y. (1989). For size markers, a RNA ladder from Bethesda Research Labs was used.

Figure 6A:
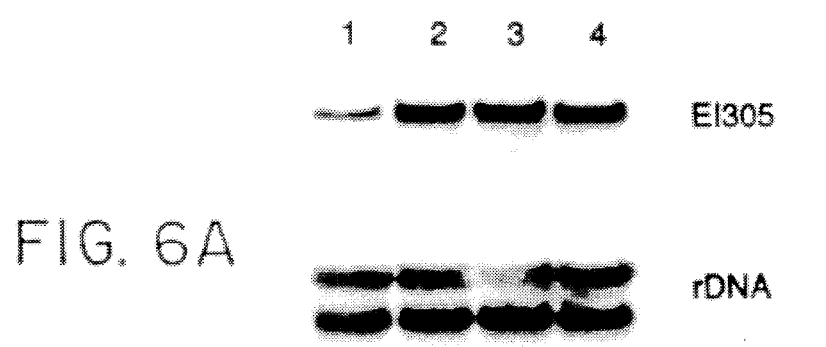
FIGS. 6A–B display a Northern analysis of ethylene-regulated transcripts.
Figure 6B:
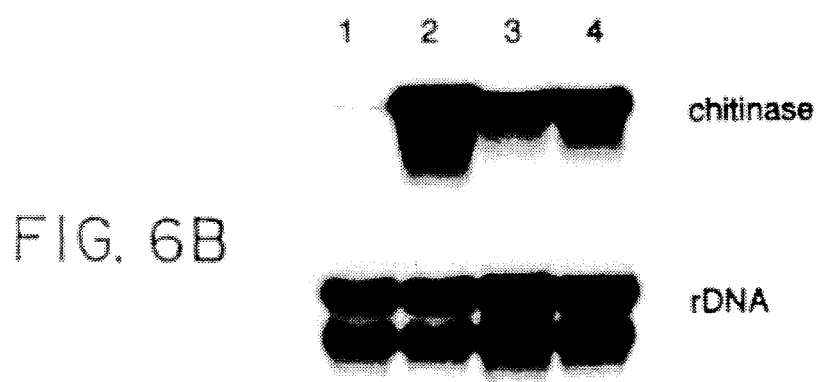

Results of the Northern analysis demonstrated that the steady state level of these ethylene-regulated genes was dramatically increased in air-grown ctrl seedlings or adult plants, see FIGS. 6A and B. The steady state level of EI305 in air-grown ctrl seedlings is comparable to wild-type plants grown in 10 μl $C_2H_4$/liter of air. The basic chitinase gene is also elevated in ctrl adults, but not to as high a level as ethylene-treated wild-type plants. This may be due to the fact that the wild-type plants are grown in air, then shifted to ethylene, whereas the ctrl mutants may be acting like plants treated continuously with ethylene.

EXAMPLE 4

Cloning the CTR1 Gene

The CTR1 was mapped to an interval between two RFLPs on the top of chromosome 5 (FIG. 3) and a chromosome walk in this area was initiated using the yUP yeast artificial chromosome (YAC) library. In parallel, a T-DNA insertional library was screened for Ctr mutants and a single line was found out of a total of 1/13,000 screened that segregated for the constitutive triple response phenotype and failed to complement ctrl-1. Genetic analysis showed that the Km[r] marker on the T-DNA was very closely linked to the ctrl mutation in this line (Table 2). The T-DNA insertion was very complex; a left border fragment detects greater than seven distinct bands in a Southern blot. The neomycin phosphotransferase (NTPII; kanamycin resistance gene from the T-DNA insert of ctrl-5 segregated at a 3:1 ratio (Km[r]:Km[s]) in progeny from a heterozygous parent. The NPTII gene within the T-DNA was mapped relative to ctrl in this line. Seedlings from a population segregating for the Ctr phenotype were screened for kanamycin resistance. Seedlings that displayed the Ctr phenotype were isolated and all (1131) were found to be resistant to kanamycin. Wild-type progeny that were resistant to kanamycin were also isolated and progeny-tested for the ctrl mutation. Of the 256 lines examined, all but a single line segregated for ctrl. Souther blot analysis suggests that this line has undergone a rearrangement of the T-DNA which may lead to efficient splicing of the intron in which the insertion resides. Taken together, these results indicate that the T-DNA was very closely linked to the ctrl mutation in this line (<1.1 cM at 95% confidence). The plant DNA flanking the site of insertion was isolated by plasmid rescue of the left border of the T-DNA.

DNA from a T3 population that was segregating for ctrl-5 was prepared by CsCl purification as described by Sambrook et al., *Molecular Cloning: A Laboratory Manual*, 2nd ed., Cold Spring Harbor Laboratory Press, Cold Spring Harbor, N.Y. (1989) and 5 μg was digested with SalI restriction enzyme. This was extracted once with an equal volume of phenol/$CHCl_3$/isoamyl alcohol (25:24:1), once with CHCl₃/isoamyl alcohol and ethanol precipitated. The DNA was resuspended in water and 5 µg was ligated in a 500 µl reaction according to the manufacturer's instructions (Promega). The ligation mix was transformed into HB101 by electroporation and plated on LB plus 100 µg/ml ampicillin (LB Amp). 500 colonies were picked into individual wells of 96 well microtiter plates containing 50 µl LB Amp and grown overnight at 37° C. The colonies were then replica plated onto a 150 mm petri plate containing LB Amp and grown overnight. Colony lifts were prepared with Hybon N+ (Amersham), and the filters probed. Nine positive colonies were obtained, four of which showed a restriction pattern that did not match that expected for an inverted repeat of T-DNA. Three of the four were identical (pCTG1) and these were then used to probe Southern blots to confirm that they contained plant DNA. The fourth isolate contained a co-cloned fragment as evidenced by the presence of an additional Sal1 site.

Figure 7A:
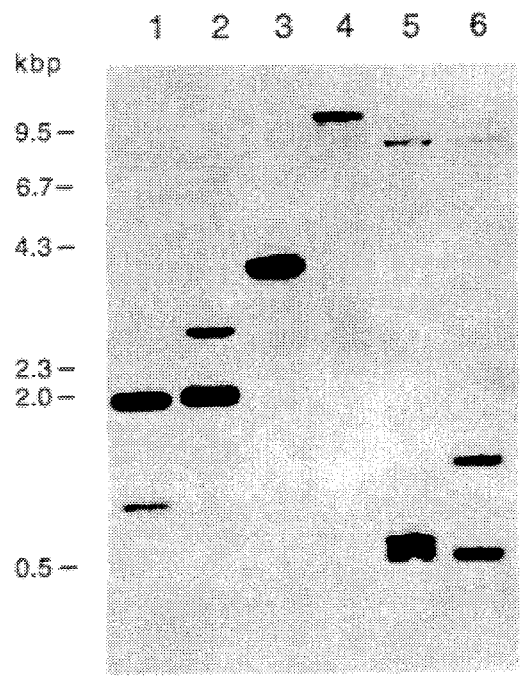
FIGS. 7A–B exhibit Southern and Northern Analysis of the CTR1 gene.

Southern blot analysis of wild-type and ctr1-5 DNA revealed that the insertional line showed an altered size of restriction fragments hybridizing to the probe indicating that the rescued DNA did indeed flank the site of T-DNA insertion, see FIG. 7A. The flanking plant DNA was used to screen genomic and cDNA libraries. The rescued plant DNA was used to isolate several lambda genomic clones and a detailed physical map of the region was constructed.

One of the genomic clones, λctg24, detected a RFLP between two different Arabidopsis ecotypes and this was used to map the cloned DNA using a population of 83 F8 recombinant inbred lines. The CTR1 gene mapped close to the RFLPs g3715 and λ217, see FIG. 3, the clones also showed complete linkage with the ctr1 mutation (0 recombinants/86 chromosomes) using DNA from a ctr1 F2 mapping population. Hybridization of RFLP probes to several Arabidopsis YAC libraries revealed that CTR1 and λ447 were contained within identical YACs, the smallest of which had an 80 kbp insert (FIG. 3). This analysis showed that the clones mapped very close to the ubq6-12-1 RFLP (1/154 recombinants), and at, or very close to the ctr1 mutation (0/78 recombinants).

Plant DNA was isolated from pCTG1 and used to probe an Arabidopsis genomic library in λEMBL (Clontech) and λDASH (gift of Dr. Nigel Crawford). Restriction maps were made of the clones, two were picked that overlapped (λctg1 and λctg24) and were in opposite orientation and these were used to probe a cDNA library constructed in λZAPII (Stratagene).

Using 5 µg poly (A)+ RNA from 3 day old dark-grown, ethylene-treated Arabidopsis seedlings (hypocotyls and cotyledons) as template and oligo d(T) as primer, first strand cDNA synthesis was catalyzed by Moloney Murine Leukemia Virus reverse transcriptase (Pharmacia). Second-strand cDNA was made as described except that DNA ligase was omitted. After the second strand reaction, the ends of the cDNA were made blunt with Klenow fragment and EcoRI/Not I adaptors (Pharmacia) were ligated to each end. The cDNA was purified from unligated adaptors by spun-column chromatography using Sephacryl S-300 and size fractionated on a 1% low melting point mini-gel. Size-selected cDNAs (0.5–1 kb, 1–2 kb, 2–3 kb, 3–6 kb) were removed from the gel using agarase (New England Biolabs), phenol:chloroform extracted and precipitated using 0.3M NaOAc (pH 7)/ethanol. A portion of each cDNA size-fraction (0.1 µg) was co-precipitated with 1 µg of λZAPII (Stratagene) EcoRI-digested, dephosphorylated arms then ligated in a volume of 4 µl overnight. Each ligation mix was packaged in vitro using a Gigapack II Gold packaging extract (Stratagene).

Clones that hybridized to both probes were picked, and all were found to be similar by restriction pattern. Thirty one of these were picked and restriction mapped, seven were sequenced from both ends and two were sequenced completely.

Figure 7B:
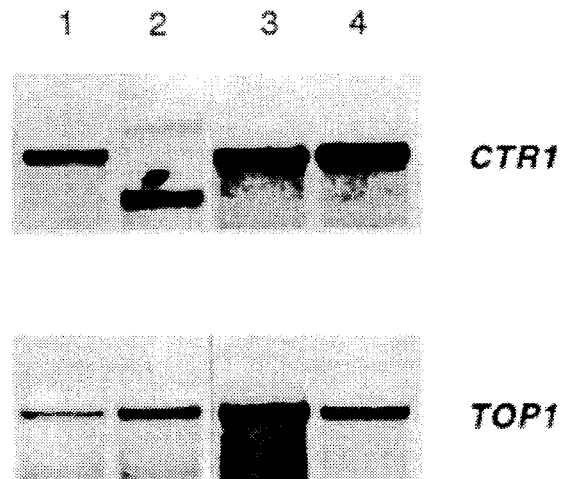

Northern blot analysis using one of the cDNA clones (λctc2-1) as a probe detected a single transcript of 3.2 kb in seedling and adult plants grown in air and ethylene, FIG. 7B. Expression of CTR1 mRNA was disrupted in the T-DNA insertion allele. The T-DNA line, ctr1-5, showed two transcripts, one larger and one smaller than the wild-type transcript, probably due to two different termination signals present in the T-DNA. The presence of two CTR1 homologous transcripts in ctr1-5 may result from termination at, or splicing to, multiple sites within the T-DNA. Alternatively, transcription initiation from a promoter close to the right border of T-DNA insertion may have resulted in expression of CTR1 sequence 3' to the insertion site. The size of the CTR1 transcript seen in the Northern blots indicates that several of the cDNA clones are near full length.

To prove that the clones did in fact represent the authentic CTR1 gene, the wild-type and several mutant alleles were sequenced, FIG. 8, FIG. 9. The cDNA and genomic clones were subcloned into pKS (Stratagene) and exonuclease III deletions were performed as described by Sambrook et al., *Molecular Cloning: A Laboratory Manual*, 2nd ed., Cold Spring Harbor Laboratory Press, Cold Spring Harbor, N.Y. (1989). DNA sequencing was done on a Applied Biosystem automated DNA sequencer (model 373A) using dye terminators as recommended by the manufacturer and also using SEQUENASE™ version 2 as described by the manufacturer (United States Biochemicals). All regions were sequenced on both stands at least one time. Synthetic oligonucleotide primers were made (18–19 bp, at least 50% GC) that would enable the exons to be sequenced. DNA was prepared from the mutant alleles by CsCl purification as described and four sets of primers were used to amplify the CTR1 gene from the mutants using the polymerase chain reaction, PCR. Internal restriction sites in the various PCR products were used to subclone the fragments into pKS and the exons sequenced using the synthetic oligonucleotides. Conditions for PCR were as follows: 35 cycles of 1' at 92° C., 1' at 55° C. and 3' at 72° C. in a Bioscycler (Bios Corp.). Taq DNA polymerase (Promega) was added after the mix was preheated to 92° C. Internal restriction sites in the various PCR products were used to subclone the fragments into pKS (Stratagene) and the exons were sequenced using primers specific for the vector (pKS) as well as gene-specific primers. Any alterations observed in the DNA sequence of the mutant alleles were re-sequenced from at least two additional independent PCR products. In one case (ctr1-4) the sequence in question was also determined from clones isolated directly from a size-selected EcoRI genomic library made in λZAPII as follows. Twenty µg of genomic DNA from ctr1-4 was cleaved to completion with EcoRI, the DNA electrophoresed through a 0.8% agarose gel and the DNA in the 1.0–1.7 kb range isolated using agarase as described by the manufacturer (New England Biolabs). The size-selected DNA was ligated into EcoRI-digested, and phosphatase-treated λZAPII (Stratagene) and the mix was packaged in vitro using Gigapack II as described by the manufacturer (Stratagene). The phage plaques were screened with a radiolabeled probe corresponding to the 1.4 kb restriction fragment which was suspected of harboring the mutation and the positive phage purified. A plasmid containing insert genomic DNA was rescued by superinfection with helper phage (R408) and the insert was sequenced as described above.

Any alterations in the mutations were re-sequenced from at least two additional independent PCR products. In two cases (ctr1-1, ctr1-4), the sequence in question was also sequenced from clones isolated directly from a sublibrary made in λZAPI.

All five of the mutant alleles are associated with sequence alterations in this gene, demonstrating conclusively that the clones correspond to the CTR1 gene. The X-ray allele, ctr1-2, SEQUENCE ID NO: 4, was due to a 17 base pair deletion beginning at position 1995 of the genomic sequence of SEQUENCE ID NO: 3 which is predicted to result in a frame shift in the coding region. One of the EMS mutants, ctr1-3, SEQUENCE ID NO: 5 was due to a C→T transition, resulting in a stop codon at position 1927 of the genomic sequence. In the resulting protein product, "arg" is converted to a stop signal. The other two alterations were single codon changes resulting in amino acid substitutions. Specifically, the ctr1-1 mutation set forth in SEQUENCE ID NO: 6 has a "T" to "A" point mutation at nucleotide position 3295 of CTR genomic DNA sequence in SEQUENCE ID NO: 3 which is predicted to result in a highly conservative substitution (Asp to Glu) at amino acid position 694. The ctr1-1 mutation of SEQUENCE ID NO: 6 was generated by DEB mutagenesis. Another mutation, ctr1-4, generated by EMS mutagenesis was also the result of a point mutation from a "G" to "A" transition at position 3233 that is predicted to result in a "Glu" to "Lys" change at amino acid 596, another invariant residue in all kinase catalytic domains, see SEQUENCE ID NO: 7. ctr1-5 comprises the T-DNA insertion found at position 3041 in intron 7 and 25 base pairs were deleted from the left border of the T-DNA at the junction with plant DNA.

The cDNA for the CTR1 gene is shown in SEQ ID NO: 1. The CTR1 gene spans approximately 6.5 kb of genomic DNA. Comparison of the cDNA and genomic clones revealed that 14 introns interrupt the CTR1 coding region and that the intron/exon boundaries all fit the consensus for splice donor and acceptor sites fairly well. The introns range in size from 77 bp to 357 bp. As determined by screening of the primary cDNA library, the longest intron (#5) is less efficiently spliced in the mRNA population. Nine of the introns are located in the carboxy-half of the gene, resulting in several very small exons; the smallest (exon #7) is only 41 base pairs. The longest open reading frame is 2466 nucleotides and predicts a protein with a molecular mass of approximately 90 kD. There are two closely spaced methionine codons at the beginning of this open reading frame, either of which could be the authentic start codon as they show reasonable correspondence to the consensus site for plant start codons. The 5' untranslated region is 117 bp in the longest cDNA, and most of the cDNA clones end within 50 base pairs of this site. The size of the 3' non-translated region varies in the different cDNAs, the longest being 453 bp. No poly(A) tail was found in any of the cDNA clones although the size of the longest cDNA matches the transcript size observed in northern blots. The upstream genomic sequence has several putative "TATA" boxes that closely match that of the plant consensus sequence. Approximately 10% (3/31) of the cDNA clones were incompletely spliced as judged by analysis of restriction enzyme digestion patterns. These may represent alternatively spliced products, although only a single transcript is detected by Northern blot analysis.

TABLE 2

Mapping of the ctr1 mutation

| Marker[a] | Progeny Type[b] | Total | Recombinants | Distance[c] |
|---|---|---|---|---|
| Morphological | | | | |
| ttg | F3 (cis) | 228 | 49 | 21.5 ± 6 |
| lu | F2 (trans) | 279 | 2 | 8.0 ± 7 |
| tt4 | F2 (cis) | 250 | 27 | 10.8 ± 3.6 |
| RFLP | | | | |
| 447 | F3[d] | 39 | 0 | 0 ± 4.7 |
| ubg 6-12-1 | F3 | 120 | 1 | 0 ± |
| 217 | | 76 | 2 | 0 ± |
| T-DNA | | | | |
| Km[r] | T3 | 1131 | O km[s] | 0 ± 5 |
| ctr | T4 from a single wt, km[r] T3 plant | 265 | 1 did not segregate ctr[e] | 0.4 m.u. ± 1.7 |

[a]Morphological markers were obtained from the Arabidopsis Stock Center. RFLP markers were kindly provided by E. Meyerwitz.
[b]Progency type form a cross of a ctr1 mutant to the marker (trans), or a cross of a line mutant for both ctr1 and the marker to wild-type (cis).
[c]Distance is shown with a 95% confidence interval.
[d]The crosses for RFLP analysis were to ecotype Niederzenz.
[e]The single non-segregating line still had T-DNA in the intron as judged by Southern analysis.

EXAMPLE 5

CTR1 is a Member of the RAF Family of Serine/Threonine Kinases

The open reading frame of the longest cDNA clone predicted a protein with a molecular weight of 90,000 containing no obvious membrane-spanning regions. A search of the PROSITE directory with the predicted CTR1 amino acid sequence reveals two signature patterns: one for an ATP binding domain IGAGSFGTV (SEQUENCE ID NO: 9) and one specific for serine/threonine protein kinases SEQUENCE ID NO: 8 (IVHRDLKSPNLLV). A search of the Swiss-prot data bank revealed that the carboxyl half of the gene was highly homologous to various protein kinases. Strong homology (>50% aa) to the Raf family of serine/threonine protein kinases was revealed in the carboxy-terminal 300 amino acids. The 11 subdomains common to all known kinases were highly conserved in the CTR1 gene and homology (49% identity in the kinase domain amino acid numbers 450 to 820) was found to the RAF family of serine/threonine kinases. The occurrence of a tyrosine at amino acid position 735 of CTR protein product resulting from nucleic acid of SEQUENCE ID NO: 2 is unique to RAF family members. The threonine at amino acid position 714 is a strong indicator that the protein is a serine/threonine, rather than a tyrosine kinase, though homology was found to the kyk1 and kyk2 genes from dictyostelium, two putative dual specificity kinases. Weak homology to the RAF genes extends an additional 300 residues upstream of the kinase domain including the presence of a serine rich region in both the RAF genes and CTR1. Also, a cystine finger is present in the 5' half of the RAF gene which is thought to bind to lipids. There is a cystine rich region in CTR1 in the appropriate position, but the spacing of the cystine residues is not consistent with known cystine finger motifs.

A FASTA search of current databases reveals significant homology in the carboxy-half (predicted catalytic domain) of the protein with over 300 known or predicted tyrosine and serine/threonine kinases. The highest degree of homology (41% identity in the kinase domain) is found with members of the Raf family of serine/threonine protein kinases. The CTR1 protein contains conserved residues in subdomain VIB, HRDLKSPN (SEQUENCE ID NO: 10), and subdomain VIII, TPEWMAPE (SEQUENCE ID NO: 11), that strongly suggest serine/threonine specificity. Interestingly, the catalytic domain of CTR1 also shows strong sequence similarity to the KYK1 gene from Dictyostelium, a putative dual specificity kinase.

There are several interesting features in the N-terminus of CTR1. The first exon (217 amino acids) is unusually rich in glycine (12.4%) and serine/threonine (19%), which is also true of the B-Raf N-terminus. There is a consensus nucleotide triphosphate binding loop or P-loop, GXXXXGKS/T where X is any residue and the last amino acid is a S or a T (SEQUENCE ID NO: 12, wherein the last amino acid is S and SEQUENCE ID NO: 13, wherein the last amino acid is T), in the N-terminal half of CTR1, starting at residue 154. This motif is thought to be involved in binding ATP or GTP in a number of proteins, including Ras, but is not generally present in protein kinases. There are also several stretches of consecutive glycine residues in the N-terminal half, a repeat cluster known as PEN, GGX, where X is any residue. Similar repeats are present in a diverse group of proteins, including B-Raf although its function is unknown.

All five ctr1 mutations disrupt the putative catalytic domain. The two amino acid substitutions seen in ctr1-1 and ctr1-4 are both in very highly conserved residues in kinases. The ctr1-1 mutation is a highly conservative aspartic acid→glutamic acid change at amino acid position 694, but this residue is invariant in all known kinases. The site of insertion of T-DNA ctr1-5, the stop codon in ctr1-3, and the 17 base pair deletion in the ctr1-2 x-ray allele are predicted to result in truncation of the CTR1 protein with loss of the kinase domain. The two amino acid substitutions seen in ctr1-1 and ctr1-4 are both in very highly conserved kinase residues. The ctr1-1 mutation is a T→A transversion at position 3295 that is predicted to result in a highly conservative substitution (Asp→Glu) at amino acid 694. However, this Asp residue is invariant in all known kinases. The change in ctr 1-4 is a G→A transition at position 3233 that is predicted to result in a Glu→Lys change at amino acid position 596, another invariant residue in all kinase catalytic domains.

EXAMPLE 6

Ethylene Production from Various Arabidopsis Strains

The amount of ethylene produced by wild-type and a number of mutants etiolated seedlings after three days in the dark was tested with a gas chromatograph in accordance with the methods of Guzman et al., supra, incorporated herein by reference. The constitutive mutants that were reversible by inhibitors of ethylene action (the Eto mutants) all significantly over-produce ethylene, ranging from 10 fold more than wild-type to over 200 fold. ctr1 mutant seedlings produced less ethylene than wild-type seedlings. The Ein mutants have been shown to produce more ethylene than wild-type seedlings. These data suggest that ethylene production is negatively regulated in Arabidopsis seedlings.

EXAMPLE 7

Molecular Analysis of Mutants

To determine whether the pEI305 cDNA is expressed and regulated by ethylene in adult plants, Northern blots containing total RNA from ethylene-treated and air-grown wild-type (wt), ctr1 and eto1 plants were hybridized with pEI305. All plants were grown in continuous light and harvested at the onset of bolting. Hormone was applied to a group of plants for 24 hours by placing them in a chamber through which 10 ppm ethylene was passed. pEI305 transcripts are barely detectable in air-grown wild-type plants, and are strongly elevated in hormone-treated plants. Air-treated eto1 adults show an increase level of transcripts relative to air-treated plants, but also show an induction upon ethylene treatment. In air-treated ctr1 adults, pEI305 transcripts are expressed at even higher levels than ethylene-treated wild-type plants, and higher levels still upon ethylene treatment.

EXAMPLE 8

Adult Phenotypes

Etiolated ctr1 seedlings grown in air were indistinguishable from etiolated wild-type seedlings grown in 10 μl $C_2H_4$/liter of air FIGS. 2A and C. When shifted to light, ctr1 seedlings opened their apical hook and expanded the cotyledons much more slowly than wild-type seedlings (24–36 hours compared to 4–5 hours for wild-type). ctr1 cotyledons were also darker green than their wild-type counterparts. Wild-type seedlings treated with ACC (an ethylene precursor) showed these same phenotypes.

Figure 2C:
Figure 2D:
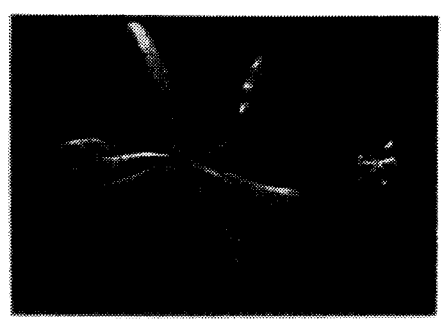

The gynoecium of ctr1 elongated significantly earlier relative to the rest of the developing flower, often protruding out of the unopened buds. A fifth allele (ctr1-5), which was generated by T-DNA insertion, showed a more severe phenotype, but this may be due to its genetic background (ctr1-5 is in the Wassilewskija ecotype while ctr1-1 through 1-4 are in the Columbia ecotype). The dramatic adult phenotype of ctr1 suggests that the gene product is involved in the ethylene response pathway of both seedlings and adult plants. The seedling phenotypes of some of these mutants grown in air is shown in FIG. 2C. A second ctr mutant (ctr2) was also identified that complements ctr1.

ctr1 adult mutants showed dramatic morphological differences compared to wild-type plants, see FIG. 2C. The mutant plants have rosette leaves that are epinastic and much smaller and darker green, they bolt approximately 1–2 weeks later, the early flowers are infertile, the root system are much less extensive and the inflorescence is much smaller than in wild-type plants. In ctr1 mutant flowers the stigmatal surface matures significantly earlier during development than in wild-type flowers. These adult phenotypes are seen in all 5 independent alleles of ctr1 and in backcrosses co-segregate 100% with ctr1. The T-DNA allele shows the most severe phenotype, though this may be due to the fact this allele was isolated in a different ecotype (WS verses Columbia for the others). The other alleles are very similar, with the exception of ctr1-3, (SEQUENCE ID NO: 5) which is slightly more infertile. The dramatic adult phenotype of ctr1 mutants suggests that this gene product is involved in the ethylene response pathway of both seedlings and adult plants.

EXAMPLE 9

Growth in Ethylene Phenocopies the ctr1 Phenotype

When adult plants are placed in ethylene, mature leaves chloros and then senesce. However, when wild-type and mutant plants were grown to maturity in the continuous presence of ethylene, they exhibited all the morphological characteristics seen in air-grown ctrl plants, with the exception that ethylene-treated plants had fewer trichomes than their air-grown counterparts. An ethylene-insensitive mutant, ein2 (Guzman et al., supra) failed to display these morphological alterations. This indicates that Arabidopsis can either adapt to the continuous presence of ethylene, or that newly formed leaves show a different response than fully formed leaves. The adult phenotype of the ctrl mutant most likely represents a constitutive adult ethylene response. Interestingly, when ctrl mutant, but not wild-type leaves, are excised and placed in the dark for several days they show significant chlorosis, approaching that seen in wild-type leaves excised and placed in ethylene in the dark.

EXAMPLE 10 ctrl Mutants Show a Reduction in the Size of Leaf Epidermal Cells

Plants were grown in chambers with air or ethylene as described above for three weeks (until just beginning to bolt). Leaves from the third or fourth true set were excised, placed in 95% ethanol and boiled for 5 minutes. The ethanol was removed, replaced with lactophenol (1:1:1:1 of 85% lactic acid, phenol, glycerol and water) and boiled again for 5 minutes. The leaves were then mounted on slides, examined under Nomarski optics and photographed. Cell sizes and shapes were quantitated by tracing photographs (10 leaves per treatment, approximately 30 cells per photograph) using a tracing tablet and the MacMeasure program, a tracing program which quantitated the reduction in cell size. The shape factor was calculated using the following equation: $SF = 4\pi A/p^2$, where A is the area and p is the perimeter.

To determine the basis for the reduction in size seen in ctrl mutant and ethylene-treated leaves, the sizes of leaf cells were examined by Nomarski microscopy. Epidermal cells from mutant leaves were significantly reduced in size relative to wild-type cells, and this reduction in cell size could be phenocopied by growth of wild-type plants in the continual presence of 1 ppm ethylene. There also was a higher concentration stomata in the mutant and ethylene-grown plants as compared to air-grown wild-type leaves, which is consistent with the hypothesis that stomata are spaced as a function of cell number, not leaf area. The reduction in the size of the epidermal cells was quantitated using a tracing program (MacMeasure), and the area of the ctrl epidermal cells was fivefold smaller than cells from air-grown wild-type plants, but indistinguishable from wild-type plants grown in ethylene (Table 3). Thus, the smaller size of ctrl and ethylene-grown wild-type leaves is due at least in part to a reduction in cell size. The ctrl mutant and ethylene-treated wild-type leaves were also rounder than wild-type leaves from air-grown plants (Table 3). This is consistent with the hypothesis that ethylene is inhibiting cell elongation, and that the ctrl mutant leaves never fully elongate, as developing unexpanded leaves are smaller and rounder than fully expanded ones.

TABLE 3

| Measurements of Epidermal Cell Size and Shape | | | |
| --- | --- | --- | --- |
| Strain | Growth[a] | Cell Area[b] | ShapeFactor[c] |
| Wild-type | Air | 3,209 ± 140 | 0.29 ± 0.008 |
| | Ethylene | 593 ± 24 | 0.69 ± 0.009 |
| ctrl | Air | 660 ± 23 | 0.63 ± 0.008 |
| | Ethylene | 830 ± 33 | 0.61 ± 0.009 |

[a]Plants were grown continuously in either blowing air or 1 µl $C_2H_4$/liter of air as described in Experimental Procedure.
[b]Mean from ten leaves, approximately 25 cells per leaf expressed in $\mu m^2$ ± the standard error.
[c]The values are from the same sample used for the area measurements, expressed as the mean ± the standard error.

EXAMPLE 11

Complementation Analysis

Complementation and linkage analysis has identified a third distinct recessive ethylene insensitivity locus, designated EIN3. As with ein1 and ein2, ein3 mutants showed insensitivity in all seedling and adult plant ethylene responses. However, unlike ein1 and ein2, genetic analysis revealed that ein3 is epistatic to the constitutive ethylene response mutation. Thus, in the ethylene action pathway of Arabidopsis, the EIN3 gene product acts down-stream of the ETR1/EIN1, EIN2, CTR1 gene products.

Two alleles of the recessive ein3 mutation have been identified. Lack of complementation between ein3-1, an EMS mutant, and ein3-2, a T-DNA insertional mutant indicate that they are allelic. The ein3-2 and ein2-1 mutations complement one another and thus define separate loci. The F2 generation of an ein1-1 (dominant mutation) X ein3-2 cross segregates wild-type progeny demonstrating that ein1 and ein3 are not allelic. However, the observed ratio of 10 mutant:1 wild-type deviates from the expected 13:3 ratio indicative of two independently assorting alleles. These results suggest that ein1 and ein3 are linked or that there is a genetic interaction between the two loci which leads to altered patterns of inheritance.

EXAMPLE 12

Overexpression of wild type CTR1 results in ethylene-insensitivity in Arabidopsis seedlings A plasmid was constructed that places the CTR1 coding sequences downstream of a CaMv 35S promotor, resulting in high level expression of CTR1 when transformed into plants. This plasmid was constructed as follows: pBI121, Jefferson et al., EMBO 1987, 6, 3901–3907, incorporated herein by reference in its entirety, containing the CaMv 35S promotor in front of a GUS gene, was cleaved with Sac1 and BamH 1, blunted with T4 DNA polymerase and religated. This step deletes the Gus gene from the plasmid and the resultant plasmid is called pBI121BS. The Xba1 fragment from pCTC2, which contains the entire CTR1 coding region and includes 26 base pairs of the CTR15' untranslated region, was then ligated into the Xba1 site of pBI121BS to give the plasmid pCT121. This construct was then transformed in Agrobacterium (strain LBA4404) and used to transform Arabidopsis roots by the method of Valvekens, PNAS 1988 85:5536–5540, incorporated herein by reference in its entirety.

Thirteen independent transformed lines were generated with pCT121. T2 seeds were collected and plated on MS plates in air or 10 ppm ethylene. Three of the thirteen independent lines fail to display a triple response in the presence of ethylene, indicating that they are insensitive to ethylene. Thus, overexpression of CTR1, a negative regulator of the Arabidopsis tthylene response pathway, results in plants that are insensitive to ethylene.

Ethylene affects a vast array of agriculturally important plant processes, including fruit ripening, flower and leaf senescence and leaf abscission. The ability to control the sensitivity of plants to ethylene could thus significantly improve the quality and longevity of many crops. The results presented here suggest that overexpression of CTR1 results in plants that do not respond to ethylene. Thus, one could control the ability of plants to respond to ethylene by controlling the expression of CTR1. These results suggest that the CTR1 gene may be extremely useful in various agriculturally important processes.

Various modifications of the invention in addition to those shown and described herein will be apparent to those skilled in the art from the foregoing description. Such modifications are also intended to fall within the scope of the appended claims.

What is claimed is:

1. A plant cell transformed to comprise the nucleic acid sequence of SEQ ID NO: 1.

2. A plant cell transformed to comprise the nucleic acid sequence of SEQ ID NO: 6.

3. A plant cell transformed to comprise the nucleic acid sequence of SEQ ID NO: 4.

4. A plant cell transformed to comprise the nucleic acid sequence of SEQ ID NO: 5.

5. A plant cell transformed to comprise the nucleic acid sequence of SEQ ID NO: 7.

6. A plant cell transformed to comprise the nucleic acid sequence of SEQ ID NO: 3 having a T-DNA insertion at position 3041.

7. A plant cell transformed to comprise a DNA sequence complementary to the nucleic acid sequence of SEQ ID NO: 1.

8. A plant cell transformed to comprise the nucleic acid sequence of SEQ ID NO: 3.

9. A plant transformed to comprise an exogenous nucleic acid sequence of SEQ ID NO: 3.

10. A plant transformed to comprise an exogenous nucleic acid sequence of SEQ ID NO: 6.

11. A plant transformed to comprise an exogenous nucleic acid sequence of SEQ ID NO: 4.

12. A plant transformed to comprise an exogenous nucleic acid sequence of SEQ ID NO: 5.

13. A plant transformed to comprise an exogenous nucleic acid sequence of SEQ ID NO: 7.

14. A plant transformed to comprise an exogenous nucleic acid sequence of SEQ ID NO: 3 having a T-DNA insertion at position 3041.

15. A plant transformed to comprise an exogenous cDNA nucleic acid sequence of SEQ ID NO: 1.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 3033 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 118..2583

( x i ) SEQUENCE DESCRIPTION: SEQ ID NO:1:

```
AGAGAAACAA GTGGCTAGCT AGCTCGCCAA ACTTCTTCAA CAATGGCGGT                    50

TTCCTAGGGT TTGATGTTTA TATGATCGGG AAACTCTCTC ATCTAGATCG                    100

CGATAACTCT CTTTTCC ATG GAA ATG CCC GGT AGA AGA TCT AAT TAC                147
                    Met Glu Met Pro Gly Arg Arg Ser Asn Tyr
                     1               5                  10

ACT TTG CTT AGT CAA TTT TCT GAC GAT CAG GTG TCA GTT TCC GTC              192
Thr Leu Leu Ser Gln Phe Ser Asp Asp Gln Val Ser Val Ser Val
                 15                  20                  25

ACC GGA GCT CCT CCG CCT CAC TAT GAT TCC TTG TCG AGC GAA AAC              237
Thr Gly Ala Pro Pro Pro His Tyr Asp Ser Leu Ser Ser Glu Asn
                 30                  35                  40

AGG AGC AAC CAT AAC AGC GGG AAC ACC GGG AAA GCT AAG GCG GAG              282
Arg Ser Asn His Asn Ser Gly Asn Thr Gly Lys Ala Lys Ala Glu
                 45                  50                  55

AGA GGC GGA TTT GAT TGG GAT CCT AGC GGT GGT GGT GGT GGT GAT              327
Arg Gly Gly Phe Asp Trp Asp Pro Ser Gly Gly Gly Gly Gly Asp
                 60                  65                  70

CAT AGG TTG AAT AAT CAA CCG AAT CGG GTT GGG AAT AAT ATG TAT              372
His Arg Leu Asn Asn Gln Pro Asn Arg Val Gly Asn Asn Met Tyr
                 75                  80                  85

GCT TCG TCT CTA GGG TTG CAA AGG CAA TCC AGT GGG AGT AGT TTC              417
Ala Ser Ser Leu Gly Leu Gln Arg Gln Ser Ser Gly Ser Ser Phe
                 90                  95                 100

GGT GAG AGC TCT TTG TCT GGG GAT TAT TAC ATG CCT ACG CTT TCT              462
Gly Glu Ser Ser Leu Ser Gly Asp Tyr Tyr Met Pro Thr Leu Ser
                105                 110                 115

GCG GCG GCT AAC GAG ATC GAA TCT GTT GGA TTT CCT CAA GAT GAT              507
Ala Ala Ala Asn Glu Ile Glu Ser Val Gly Phe Pro Gln Asp Asp
                120                 125                 130
```

```
GGG TTT AGG CTT GGA TTT GGT GGT GGT GGA GGA GAT TTG AGG ATA    552
Gly Phe Arg Leu Gly Phe Gly Gly Gly Gly Gly Asp Leu Arg Ile
            135             140             145

CAG ATG GCG GCG GAC TCC GCT GGA GGG TCT TCA TCT GGG AAG AGC    597
Gln Met Ala Ala Asp Ser Ala Gly Gly Ser Ser Ser Gly Lys Ser
            150             155             160

TGG GCG CAG CAG ACG GAG GAG AGT TAT CAG CTG CAG CTT GCA TTG    642
Trp Ala Gln Gln Thr Glu Glu Ser Tyr Gln Leu Gln Leu Ala Leu
            165             170             175

GCG TTA AGG CTT TCG TCG GAG GCT ACT TGT GCC GAC GAT CCG AAC    687
Ala Leu Arg Leu Ser Ser Glu Ala Thr Cys Ala Asp Asp Pro Asn
            180             185             190

TTT CTG GAT CCT GTA CCG GAC GAG TCT GCT TTA CGG ACT TCG CCA    732
Phe Leu Asp Pro Val Pro Asp Glu Ser Ala Leu Arg Thr Ser Pro
            195             200             205

AGT TCA GCC GAA ACC GTT TCA CAT CGT TTC TGG GTT AAT GGC TGC    777
Ser Ser Ala Glu Thr Val Ser His Arg Phe Trp Val Asn Gly Cys
            210             215             220

TTA TCG TAC TAT GAT AAA GTT CCT GAT GGG TTT TAT ATG ATG AAT    822
Leu Ser Tyr Tyr Asp Lys Val Pro Asp Gly Phe Tyr Met Met Asn
            225             230             235

GGT CTG GAT CCC TAT ATT TGG ACC TTA TGC ATC GAC CTG CAT GAA    867
Gly Leu Asp Pro Tyr Ile Trp Thr Leu Cys Ile Asp Leu His Glu
            240             245             250

AGT GGT CGC ATC CCT TCA ATT GAA TCA TTA AGA GCT GTT GAT TCT    912
Ser Gly Arg Ile Pro Ser Ile Glu Ser Leu Arg Ala Val Asp Ser
            255             260             265

GGT GTT GAT TCT TCG CTT GAA GCG ATC ATA GTT GAT AGG CGT AGT    957
Gly Val Asp Ser Ser Leu Glu Ala Ile Ile Val Asp Arg Arg Ser
            270             275             280

GAT CCA GCC TTC AAG GAA CTT CAC AAT AGA GTC CAC GAC ATA TCT   1002
Asp Pro Ala Phe Lys Glu Leu His Asn Arg Val His Asp Ile Ser
            285             290             295

TGT AGC TGC ATT ACC ACA AAA GAG GTT GTT GAT CAG CTG GCA AAG   1047
Cys Ser Cys Ile Thr Thr Lys Glu Val Val Asp Gln Leu Ala Lys
            300             305             310

CTT ATC TGC AAT CGT ATG GGG GGT CCA GTT ATC ATG GGG GAA GAT   1092
Leu Ile Cys Asn Arg Met Gly Gly Pro Val Ile Met Gly Glu Asp
            315             320             325

GAG TTG GTT CCC ATG TGG AAG GAG TGC ATT GAT GGT CTA AAA GAA   1137
Glu Leu Val Pro Met Trp Lys Glu Cys Ile Asp Gly Leu Lys Glu
            330             335             340

ATC TTT AAA GTG GTG GTT CCC ATA GGT AGC CTC TCT GTT GGA CTC   1182
Ile Phe Lys Val Val Val Pro Ile Gly Ser Leu Ser Val Gly Leu
            345             350             355

TGC AGA CAT CGA GCT TTA CTC TTC AAA GTA CTG GCT GAC ATA ATT   1227
Cys Arg His Arg Ala Leu Leu Phe Lys Val Leu Ala Asp Ile Ile
            360             365             370

GAT TTA CCC TGT CGA ATT GCC AAA GGA TGT AAA TAT TGT AAT AGA   1272
Asp Leu Pro Cys Arg Ile Ala Lys Gly Cys Lys Tyr Cys Asn Arg
            375             380             385

GAC GAT GCC GCT TCG TGC CTT GTC AGG TTT GGG CTT GAT AGG GAG   1317
Asp Asp Ala Ala Ser Cys Leu Val Arg Phe Gly Leu Asp Arg Glu
            390             395             400

TAC CTG GTT GAT TTA GTA GGA AAG CCA GGT CAC TTA TGG GAG CCT   1362
Tyr Leu Val Asp Leu Val Gly Lys Pro Gly His Leu Trp Glu Pro
            405             410             415

GAT TCC TTG CTA AAT GGT CCT TCA TCT ATC TCA ATT TCT TCT CCT   1407
Asp Ser Leu Leu Asn Gly Pro Ser Ser Ile Ser Ile Ser Ser Pro
            420             425             430
```

```
CTG CGG TTT CCA CGA CCA AAG CCA GTT GAA CCC GCA GTC GAT TTT    1452
Leu Arg Phe Pro Arg Pro Lys Pro Val Glu Pro Ala Val Asp Phe
            435             440                     445

AGG TTA CTA GCC AAA CAA TAT TTC TCC GAT AGC CAG TCT CTT AAT    1497
Arg Leu Leu Ala Lys Gln Tyr Phe Ser Asp Ser Gln Ser Leu Asn
            450             455                     460

CTT GTT TTC GAT CCT GCA TCA GAT GAT ATG GGA TTC TCA ATG TTT    1542
Leu Val Phe Asp Pro Ala Ser Asp Asp Met Gly Phe Ser Met Phe
            465             470                     475

CAT AGG CAA TAT GAT AAT CCG GGT GGA GAG AAT GAC GCA TTG GCA    1587
His Arg Gln Tyr Asp Asn Pro Gly Gly Glu Asn Asp Ala Leu Ala
            480             485                     490

GAA AAT GGT GGT GGG TCT TTG CCA CCC AGT GCT AAT ATG CCT CCA    1632
Glu Asn Gly Gly Gly Ser Leu Pro Pro Ser Ala Asn Met Pro Pro
            495             500                     505

CAG AAC ATG ATG CGT GCG TCA AAT CAA ATT GAA GCA GCA CCT ATG    1677
Gln Asn Met Met Arg Ala Ser Asn Gln Ile Glu Ala Ala Pro Met
            510             515                     520

AAT GCC CCA CCA ATC AGT CAG CCA GTT CCA AAC AGG GCA AAT AGG    1722
Asn Ala Pro Pro Ile Ser Gln Pro Val Pro Asn Arg Ala Asn Arg
            525             530                     535

GAA CTT GGA CTT GAT GGT GAT GAT ATG GAC ATC CCG TGG TGT GAT    1767
Glu Leu Gly Leu Asp Gly Asp Asp Met Asp Ile Pro Trp Cys Asp
            540             545                     550

CTT AAT ATA AAA GAA AAG ATT GGA GCA GGT TCC TTT GGC ACT GTC    1812
Leu Asn Ile Lys Glu Lys Ile Gly Ala Gly Ser Phe Gly Thr Val
            555             560                     565

CAC CGT GCT GAG TGG CAT GGC TCG GAT GTT GCT GTG AAA ATT CTC    1857
His Arg Ala Glu Trp His Gly Ser Asp Val Ala Val Lys Ile Leu
            570             575                     580

ATG GAG CAA GAC TTC CAT GCT GAG CGT GTT AAT GAG TTC TTA AGA    1902
Met Glu Gln Asp Phe His Ala Glu Arg Val Asn Glu Phe Leu Arg
            585             590                     595

GAG GTT GCG ATA ATG AAA CGC CTT CGC CAC CCT AAC ATT GTT CTC    1947
Glu Val Ala Ile Met Lys Arg Leu Arg His Pro Asn Ile Val Leu
            600             605                     610

TTC ATG GGT GCG GTC ACT CAA CCT CCA AAT TTG TCA ATA GTG ACA    1992
Phe Met Gly Ala Val Thr Gln Pro Pro Asn Leu Ser Ile Val Thr
            615             620                     625

GAA TAT TTG TCA AGA GGT AGT TTA TAC AGA CTT TTG CAT AAA AGT    2037
Glu Tyr Leu Ser Arg Gly Ser Leu Tyr Arg Leu Leu His Lys Ser
            630             635                     640

GGA GCA AGG GAG CAA TTA GAT GAG AGA CGT CGC CTG AGT ATG GCT    2082
Gly Ala Arg Glu Gln Leu Asp Glu Arg Arg Arg Leu Ser Met Ala
            645             650                     655

TAT GAT GTG GCT AAG GGA ATG AAT TAT CTT CAC AAT CGC AAT CCT    2127
Tyr Asp Val Ala Lys Gly Met Asn Tyr Leu His Asn Arg Asn Pro
            660             665                     670

CCA ATT GTG CAT AGA GAT CTA AAA TCT CCA AAC TTA TTG GTT GAC    2172
Pro Ile Val His Arg Asp Leu Lys Ser Pro Asn Leu Leu Val Asp
            675             680                     685

AAA AAA TAT ACA GTC AAG GTT TGT GAT TTT GGT CTC TCG CGA TTG    2217
Lys Lys Tyr Thr Val Lys Val Cys Asp Phe Gly Leu Ser Arg Leu
            690             695                     700

AAG GCC AGC ACG TTT CTT TCC TCG AAG TCA GCA GCT GGA ACC CCC    2262
Lys Ala Ser Thr Phe Leu Ser Ser Lys Ser Ala Ala Gly Thr Pro
            705             710                     715

GAG TGG ATG GCA CCA GAA GTC CTG CGA GAT GAG CCG TCT AAT GAA    2307
Glu Trp Met Ala Pro Glu Val Leu Arg Asp Glu Pro Ser Asn Glu
            720             725                     730
```

-continued

| | | | | | | | | | | | | | | | |
|---|---|---|---|---|---|---|---|---|---|---|---|---|---|---|---|
| AAG | TCA | GAT | GTG | TAC | AGC | TTC | GGG | GTC | ATC | TTG | TGG | GAG | CTT | GCT | 2352 |
| Lys | Ser | Asp | Val | Tyr 735 | Ser | Phe | Gly | Val | Ile 740 | Leu | Trp | Glu | Leu | Ala 745 | |
| ACA | TTG | CAA | CAA | CCA | TGG | GGT | AAC | TTA | AAT | CCG | GCT | CAG | GTT | GTA | 2397 |
| Thr | Leu | Gln | Gln | Pro 750 | Trp | Gly | Asn | Leu | Asn 755 | Pro | Ala | Gln | Val | Val 760 | |
| GCT | GCG | GTT | GGT | TTC | AAG | TGT | AAA | CGG | CTG | GAG | ATC | CCG | CGT | AAT | 2442 |
| Ala | Ala | Val | Gly | Phe 765 | Lys | Cys | Lys | Arg | Leu 770 | Glu | Ile | Pro | Arg | Asn 775 | |
| CTG | AAT | CCT | CAG | GTT | GCA | GCC | ATA | ATC | GAG | GGT | TGT | TGG | ACC | AAT | 2487 |
| Leu | Asn | Pro | Gln | Val 780 | Ala | Ala | Ile | Ile | Glu 785 | Gly | Cys | Trp | Thr | Asn 790 | |
| GAG | CCA | TGG | AAG | CGT | CCA | TCA | TTT | GCA | ACT | ATA | ATG | GAC | TTG | CTA | 2532 |
| Glu | Pro | Trp | Lys | Arg 795 | Pro | Ser | Phe | Ala | Thr 800 | Ile | Met | Asp | Leu | Leu 805 | |
| AGA | CCA | TTG | ATC | AAA | TCA | GCG | GTT | CCT | CCG | CCC | AAC | CGC | TCG | GAT | 2577 |
| Arg | Pro | Leu | Ile | Lys 810 | Ser | Ala | Val | Pro | Pro 815 | Pro | Asn | Arg | Ser | Asp 820 | |

| | | | | | |
|---|---|---|---|---|---|
| TTG | TAAATACCC | CCGGTCCATT | CAAAAGTTGT | TATAATCATG | ATATGCACAT | 2630 |
| Leu | | | | | | |
| ATACTCTCAG | CATTCTTTTG | CTGCCCAGGA | GGGAGACACT | AGTTAAGATA | | 2680 |
| TAGCTTTAAA | GGTACATTCC | TCATGAGCTA | TCAATCATAT | CCTACAGAAT | | 2730 |
| CCCATGGTTT | TTATACATGT | ATTATTTTTG | CGATCTTTGT | CTGCTGTTTT | | 2780 |
| GTTCCCTTTT | TAATGTTGCA | GATTGTTAAA | ATGTACATGA | CTATTGTCAC | | 2830 |
| AGGGAGGAAA | AAAAAATGTA | GTAATGGAAA | CAATGTGAGG | GATATAATCT | | 2880 |
| ATCTATCTAG | TCCCAAGGG | TAAGCAATAT | TGTGTTGTTA | TGTCTTTGTA | | 2930 |
| GCAATGCACT | GAAAGCTATA | TTTAATTACA | TTGCTGTACA | TTTATACCGC | | 2980 |
| TAAATTAGTT | ACTAAGCGAA | GGTAAAAAAG | AGCAGCTGGT | AAATGCTGTC | | 3030 |
| AAA | | | | | | 3033 |

(2) INFORMATION FOR SEQ ID NO:2:

(i) SEQUENCE CHARACTERISTICS:
        (A) LENGTH: 821 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met 1 | Glu | Met | Pro | Gly 5 | Arg | Arg | Ser | Asn | Tyr 10 | Thr | Leu | Leu | Ser | Gln Phe 15 |
| Ser | Asp | Asp | Gln 20 | Val | Ser | Val | Ser | Val 25 | Thr | Gly | Ala | Pro | Pro 30 | Pro His |
| Tyr | Asp | Ser | Leu 35 | Ser | Ser | Glu | Asn | Arg 40 | Ser | Asn | His | Asn 45 | Ser | Gly Asn |
| Thr | Gly 50 | Lys | Ala | Lys | Ala | Glu 55 | Arg | Gly | Gly | Phe | Asp 60 | Trp | Asp | Pro Ser |
| Gly 65 | Gly | Gly | Gly | Gly | Asp 70 | His | Arg | Leu | Asn | Asn 75 | Gln | Pro | Asn | Arg Val 80 |
| Gly | Asn | Asn | Met | Tyr 85 | Ala | Ser | Ser | Leu | Gly 90 | Leu | Gln | Arg | Gln | Ser Ser 95 |
| Gly | Ser | Ser | Phe 100 | Gly | Glu | Ser | Ser | Leu 105 | Ser | Gly | Asp | Tyr | Tyr 110 | Met Pro |
| Thr | Leu | Ser 115 | Ala | Ala | Ala | Asn | Glu 120 | Ile | Glu | Ser | Val | Gly 125 | Phe | Pro Gln |

| | | | | | | | | | | | | | | |
|---|---|---|---|---|---|---|---|---|---|---|---|---|---|---|
| Asp | Asp | Gly | Phe | Arg | Leu | Gly | Phe | Gly | Gly | Gly | Gly | Asp | Leu | Arg |
| | 130 | | | | | 135 | | | | 140 | | | | |
| Ile | Gln | Met | Ala | Ala | Asp | Ser | Ala | Gly | Gly | Ser | Ser | Ser | Gly | Lys | Ser |
| 145 | | | | | 150 | | | | | 155 | | | | | 160 |
| Trp | Ala | Gln | Gln | Thr | Glu | Glu | Ser | Tyr | Gln | Leu | Gln | Leu | Ala | Leu | Ala |
| | | | | 165 | | | | | 170 | | | | | 175 | |
| Leu | Arg | Leu | Ser | Ser | Glu | Ala | Thr | Cys | Ala | Asp | Asp | Pro | Asn | Phe | Leu |
| | | | 180 | | | | | 185 | | | | | 190 | | |
| Asp | Pro | Val | Pro | Asp | Glu | Ser | Ala | Leu | Arg | Thr | Ser | Pro | Ser | Ser | Ala |
| | | 195 | | | | | 200 | | | | | 205 | | | |
| Glu | Thr | Val | Ser | His | Arg | Phe | Trp | Val | Asn | Gly | Cys | Leu | Ser | Tyr | Tyr |
| | 210 | | | | | 215 | | | | | 220 | | | | |
| Asp | Lys | Val | Pro | Asp | Gly | Phe | Tyr | Met | Met | Asn | Gly | Leu | Asp | Pro | Tyr |
| 225 | | | | | 230 | | | | | 235 | | | | | 240 |
| Ile | Trp | Thr | Leu | Cys | Ile | Asp | Leu | His | Glu | Ser | Gly | Arg | Ile | Pro | Ser |
| | | | | 245 | | | | | 250 | | | | | 255 | |
| Ile | Glu | Ser | Leu | Arg | Ala | Val | Asp | Ser | Gly | Val | Asp | Ser | Ser | Leu | Glu |
| | | | 260 | | | | | 265 | | | | | 270 | | |
| Ala | Ile | Ile | Val | Asp | Arg | Arg | Ser | Asp | Pro | Ala | Phe | Lys | Glu | Leu | His |
| | | 275 | | | | | 280 | | | | | 285 | | | |
| Asn | Arg | Val | His | Asp | Ile | Ser | Cys | Ser | Cys | Ile | Thr | Thr | Lys | Glu | Val |
| | 290 | | | | | 295 | | | | | 300 | | | | |
| Val | Asp | Gln | Leu | Ala | Lys | Leu | Ile | Cys | Asn | Arg | Met | Gly | Gly | Pro | Val |
| 305 | | | | | 310 | | | | | 315 | | | | | 320 |
| Ile | Met | Gly | Glu | Asp | Glu | Leu | Val | Pro | Met | Trp | Lys | Glu | Cys | Ile | Asp |
| | | | | 325 | | | | | 330 | | | | | 335 | |
| Gly | Leu | Lys | Glu | Ile | Phe | Lys | Val | Val | Pro | Ile | Gly | Ser | Leu | Ser |
| | | | 340 | | | | | 345 | | | | | 350 | | |
| Val | Gly | Leu | Cys | Arg | His | Arg | Ala | Leu | Leu | Phe | Lys | Val | Leu | Ala | Asp |
| | | 355 | | | | | 360 | | | | | 365 | | | |
| Ile | Ile | Asp | Leu | Pro | Cys | Arg | Ile | Ala | Lys | Gly | Cys | Lys | Tyr | Cys | Asn |
| | 370 | | | | | 375 | | | | | 380 | | | | |
| Arg | Asp | Asp | Ala | Ala | Ser | Cys | Leu | Val | Arg | Phe | Gly | Leu | Asp | Arg | Glu |
| 385 | | | | | 390 | | | | | 395 | | | | | 400 |
| Tyr | Leu | Val | Asp | Leu | Val | Gly | Lys | Pro | Gly | His | Leu | Trp | Glu | Pro | Asp |
| | | | | 405 | | | | | 410 | | | | | 415 | |
| Ser | Leu | Leu | Asn | Gly | Pro | Ser | Ser | Ile | Ser | Ile | Ser | Ser | Pro | Leu | Arg |
| | | | 420 | | | | | 425 | | | | | 430 | | |
| Phe | Pro | Arg | Pro | Lys | Pro | Val | Glu | Pro | Ala | Val | Asp | Phe | Arg | Leu | Leu |
| | | 435 | | | | | 440 | | | | | 445 | | | |
| Ala | Lys | Gln | Tyr | Phe | Ser | Asp | Ser | Gln | Ser | Leu | Asn | Leu | Val | Phe | Asp |
| | 450 | | | | | 455 | | | | | 460 | | | | |
| Pro | Ala | Ser | Asp | Asp | Met | Gly | Phe | Ser | Met | Phe | His | Arg | Gln | Tyr | Asp |
| 465 | | | | | 470 | | | | | 475 | | | | | 480 |
| Asn | Pro | Gly | Gly | Glu | Asn | Asp | Ala | Leu | Ala | Glu | Asn | Gly | Gly | Ser |
| | | | | 485 | | | | | 490 | | | | | 495 | |
| Leu | Pro | Pro | Ser | Ala | Asn | Met | Pro | Pro | Gln | Asn | Met | Met | Arg | Ala | Ser |
| | | | 500 | | | | | 505 | | | | | 510 | | |
| Asn | Gln | Ile | Glu | Ala | Ala | Pro | Met | Asn | Ala | Pro | Pro | Ile | Ser | Gln | Pro |
| | | 515 | | | | | 520 | | | | | 525 | | | |
| Val | Pro | Asn | Arg | Ala | Asn | Arg | Glu | Leu | Gly | Leu | Asp | Gly | Asp | Asp | Met |
| | 530 | | | | | 535 | | | | | 540 | | | | |
| Asp | Ile | Pro | Trp | Cys | Asp | Leu | Asn | Ile | Lys | Glu | Lys | Ile | Gly | Ala | Gly |

-continued

| | | | | 545 | | | | | 550 | | | | | 555 | | | | | 560 |
|---|---|---|---|---|---|---|---|---|---|---|---|---|---|---|---|---|---|---|---|
| Ser | Phe | Gly | Thr | Val | His | Arg | Ala | Glu | Trp | His | Gly | Ser | Asp | Val | Ala |
| | | | | 565 | | | | | 570 | | | | | 575 | |
| Val | Lys | Ile | Leu | Met | Glu | Gln | Asp | Phe | His | Ala | Glu | Arg | Val | Asn | Glu |
| | | | | 580 | | | | | 585 | | | | | 590 | |
| Phe | Leu | Arg | Glu | Val | Ala | Ile | Met | Lys | Arg | Leu | Arg | His | Pro | Asn | Ile |
| | | | 595 | | | | | 600 | | | | | 605 | | |
| Val | Leu | Phe | Met | Gly | Ala | Val | Thr | Gln | Pro | Pro | Asn | Leu | Ser | Ile | Val |
| | | 610 | | | | | 615 | | | | | 620 | | | |
| Thr | Glu | Tyr | Leu | Ser | Arg | Gly | Ser | Leu | Tyr | Arg | Leu | Leu | His | Lys | Ser |
| 625 | | | | | 630 | | | | | 635 | | | | | 640 |
| Gly | Ala | Arg | Glu | Gln | Leu | Asp | Glu | Arg | Arg | Arg | Leu | Ser | Met | Ala | Tyr |
| | | | | 645 | | | | | 650 | | | | | 655 | |
| Asp | Val | Ala | Lys | Gly | Met | Asn | Tyr | Leu | His | Asn | Arg | Asn | Pro | Pro | Ile |
| | | | 660 | | | | | 665 | | | | | 670 | | |
| Val | His | Arg | Asp | Leu | Lys | Ser | Pro | Asn | Leu | Leu | Val | Asp | Lys | Lys | Tyr |
| | | 675 | | | | | 680 | | | | | 685 | | | |
| Thr | Val | Lys | Val | Cys | Asp | Phe | Gly | Leu | Ser | Arg | Leu | Lys | Ala | Ser | Thr |
| | 690 | | | | | 695 | | | | | 700 | | | | |
| Phe | Leu | Ser | Ser | Lys | Ser | Ala | Ala | Gly | Thr | Pro | Glu | Trp | Met | Ala | Pro |
| 705 | | | | | 710 | | | | | 715 | | | | | 720 |
| Glu | Val | Leu | Arg | Asp | Glu | Pro | Ser | Asn | Glu | Lys | Ser | Asp | Val | Tyr | Ser |
| | | | | 725 | | | | | 730 | | | | | 735 | |
| Phe | Gly | Val | Ile | Leu | Trp | Glu | Leu | Ala | Thr | Leu | Gln | Gln | Pro | Trp | Gly |
| | | | 740 | | | | | 745 | | | | | 750 | | |
| Asn | Leu | Asn | Pro | Ala | Gln | Val | Val | Ala | Ala | Val | Gly | Phe | Lys | Cys | Lys |
| | | 755 | | | | | 760 | | | | | 765 | | | |
| Arg | Leu | Glu | Ile | Pro | Arg | Asn | Leu | Asn | Pro | Gln | Val | Ala | Ala | Ile | Ile |
| | 770 | | | | | 775 | | | | | 780 | | | | |
| Glu | Gly | Cys | Trp | Thr | Asn | Glu | Pro | Trp | Lys | Arg | Pro | Ser | Phe | Ala | Thr |
| 785 | | | | | 790 | | | | | 795 | | | | | 800 |
| Ile | Met | Asp | Leu | Leu | Arg | Pro | Leu | Ile | Lys | Ser | Ala | Val | Pro | Pro | Pro |
| | | | | 805 | | | | | 810 | | | | | 815 | |
| Asn | Arg | Ser | Asp | Leu | | | | | | | | | | | |
| | | | 820 | | | | | | | | | | | | |

( 2 ) INFORMATION FOR SEQ ID NO:3:

( i ) SEQUENCE CHARACTERISTICS:
        ( A ) LENGTH: 6312 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| TATAGTCCAT | TCTCTCACTT | TCTATTCTAA | ATATTGTGGA | CGTTATAAAG | 50 |
| GCTTTTTATT | TATTTTATGT | CGAGTTTTTT | AGACTACGTA | GAGCCGAATG | 100 |
| AAAATTTCAT | GTTAGGTAT | ACGAAACTTG | GATCCAATGT | TACGGATTCA | 150 |
| GATTGGTGTA | AAAGATCAAA | TTTGATAGTA | TTTGGATTTG | ATAGGCAAGA | 200 |
| TGGTTTAGTA | TTTTACACTG | TGTATGTTCC | TCTTTTAGCT | TTGCGTTTTC | 250 |
| TACTTTCACT | ACGATACTAC | TTTTTATCTT | CCAATTTCAG | TTGCTTATCA | 300 |
| CCAAAATATG | AAATACCAAA | TTAATTGTTT | AAACAGTTTT | ATTAGCGATT | 350 |

```
AAATTAGCAC  AAAACATATG  AATAGATATC  ATAGTCGAAT  ACAAAAATTA     400
GACAAATAAT  AATACACTAA  AAAACAAACT  AAATTGGAGA  ATTGTTTTGA     450
CAAAAAATAA  AAAAAATGTC  AAAGTTCCAT  AAAAAGGAGG  ACAAAGAGG      500
AATATAACGA  AATTATCAAC  AGAAACGCAC  CGAGTAAGTT  TATTTCCTAT     550
GATAACGCAA  AAACAAAAAA  AAAATCCAAT  TCCATTAGAG  AGAGAGAGAG     600
AGAGAGAGAG  AGAGAGAGAC  TTTTTTAGAA  AGTACACAAA  AAAAATGAAA     650
AACTAGAGAG  AGAAACAAGT  GGCTAGCTAG  CTCGCCAAAC  TTCTTCAACA     700
ATGGCGGTTT  CCTAGGGTTT  GATGTTTATA  TGATCGGGAA  ACTCTCTCAT     750
CTAGATCGCG  ATAACTCTCT  TTTCCATGGA  AATGCCCGGT  AGAAGATCTA     800
ATTACACTTT  GCTTAGTCAA  TTTTCTGACG  ATCAGGTGTC  AGTTTCCGTC     850
ACCGGAGCTC  CTCCGCCTCA  CTATGATTCC  TTGTCGAGCG  AAAACAGGAG     900
CAACCATAAC  AGCGGGAACA  CCGGGAAAGC  TAAGGCGGAG  AGAGGCGGAT     950
TTGATTGGGA  TCCTAGCGGT  GGTGGTGGTG  GTGATCATAG  GTTGAATAAT    1000
CAACCGAATC  GGGTTGGGAA  TAATATGTAT  GCTTCGTCTC  TAGGGTTGCA    1050
AAGGCAATCC  AGTGGGAGTA  GTTTCGGTGA  GAGCTCTTTG  TCTGGGGATT    1100
ATTACATGCC  TACGCTTTCT  GCGGCGGCTA  ACGAGATCGA  ATCTGTTGGA    1150
TTTCCTCAAG  ATGATGGGTT  TAGGCTTGGA  TTTGGTGGTG  GTGGAGGAGA    1200
TTTGAGGATA  CAGATGGCGG  CGGACTCCGC  TGGAGGGTCT  TCATCTGGGA    1250
AGAGCTGGGC  GCAGCAGACG  GAGGAGAGTT  ATCAGCTGCA  GCTTGCATTG    1300
GCGTTAAGGC  TTTCGTCGGA  GGCTACTTGT  GCCGACGATC  CGAACTTTCT    1350
GGATCCTGTA  CCGGACGAGT  CTGCTTTACG  GACTTCGCCA  AGTTCAGCCG    1400
AAACCGTTTC  ACATCGTTTC  TGGGTATTTG  TTCCTGTTAA  GCTTTGTTTC    1450
CCAAAATTAT  TGAATCGTGG  TTATAGAGAT  ATGGTCCTCT  TGTTTCCGAA    1500
GTTTCAGTTA  GATCTCCTTA  CCAAAAGTCT  ATTAGTAGCA  AATGAGATAT    1550
GTTGTTTAGA  TACATTGCAG  AGTATGATTG  TTTTGTGTGC  TGCATCAGGT    1600
TAATGGCTGC  TTATCGTACT  ATGATAAAGT  TCCTGATGGG  TTTTATATGA    1650
TGAATGGTCT  GGATCCCTAT  ATTTGGACCT  TATGCATCGA  CCTGCATGAA    1700
AGTGGTCGCA  TCCCTTCAAT  TGAATCATTA  AGAGCTGTTG  ATTCTGGTGT    1750
TGATTCTTCG  CTTGAAGCGA  TCATAGTTGA  TAGGCGTAGT  GATCCAGCCT    1800
TCAAGGAACT  TCACAATAGA  GTCCACGACA  TATCTTGTAG  CTGCATTACC    1850
ACAAAGAGG   TTGTTGATCA  GCTGGCAAAG  CTTATCTGCA  ATCGTATGGG    1900
GTTTGTACTC  ATACAATCCT  TACTATCCCT  TGAACTTAT   ATTTTTATAT    1950
CTTCCTGTGA  TTTCTCACAT  TGTACTCGTT  AATTCTTGCT  TCCCCAGGGG    2000
TCCAGTTATC  ATGGGGGAAG  ATGAGTTGGT  TCCCATGTGG  AAGGAGTGCA    2050
TTGATGGTCT  AAAAGAAATC  TTTAAAGTGG  TGGTTCCCAT  AGGTAGCCTC    2100
TCTGTTGGAC  TCTGCAGACA  TCGAGCTTTA  CTCTTCAAAG  TGAGATCCCA    2150
ACTTTGATGC  TATCCCCATG  ACATTTAAGA  CATCTTGTGA  AATGATCATA    2200
TAAATTATTG  TGCTTCATCC  ATTTGTTTTT  ATTGGAATAC  ATATGAAGAA    2250
CGTTGAATGT  GAAAAGTGGT  GTTATTGATT  AGAAAAAAAT  AGGTTACTGA    2300
TAGTTGAATG  TTCCAAAGAA  AAAAAGTATT  TTATATCTTC  TATTTGGTGC    2350
```

| | | | | |
|---|---|---|---|---|
| ATGCAGGTAC | TGGCTGACAT | AATTGATTTA | CCCTGTCGAA | TTGCCAAAGG | 2400 |
| ATGTAAATAT | TGTAATAGAG | ACGATGCCGC | TTCGTGCCTT | GTCAGGTTTG | 2450 |
| GGCTTGATAG | GTATGATACA | AGTGATTGCG | AAAGAGCCTT | TATTTTCCTA | 2500 |
| TTTTCTTTGC | TTTTTGTTTC | TGGAAAAACA | ATTATAGCTC | CAAATGTTTC | 2550 |
| GCAGAATATT | AGGTTGATGA | CGTGGAAAAT | TTGTTTTGGT | TTCAGGGAGT | 2600 |
| ACCTGGTTGA | TTTAGTAGGA | AAGCCAGGTC | ACTTATGGGA | GCCTGATTCC | 2650 |
| TTGCTAAATG | GTCCTTCATC | TATCTCAATT | TCTTCTCCTC | TGCGGTTTCC | 2700 |
| ACGACCAAAG | CCAGTTGAAC | CCGCAGTCGA | TTTAGGTTA | CTAGCCAAAC | 2750 |
| AATATTTCTC | CGATAGCCAG | TCTCTTAATC | TTGTTTTCGA | TCCTGCATCA | 2800 |
| GGTATTCCCA | TACAAAAAAC | CTAAATAATA | TGTTAACTTT | TGCATGCTG | 2850 |
| CTTACATCTC | GTTTTGTATT | TCCCTAAAA | GAGTAATCTC | CTATCATTTA | 2900 |
| GGGTATTTCT | TGATCATGTC | TCAGTATCTG | AAGTGTTAGT | AGTCTTAGAA | 2950 |
| TGATTCTATT | GTTTGTTTTC | TTGTCTCTTT | TCACTTTAGT | TGTTTTGGC | 3000 |
| TGTTGATGTG | TATGTTTGTT | GGTGGGTTCT | TTGCCTAATG | ATATTTAAGG | 3050 |
| TTAAACTTGT | TAGTCTGCTG | TTCAAGCTTA | TGAATTCTAG | TGCATTTATG | 3100 |
| TGCAAGACTT | GTCTTCTGGA | CTCTAATTTC | TTATATCTGC | TTGTTTGAAT | 3150 |
| GGTTGTAGAT | GATATGGGAT | TCTCAATGTT | TCATAGGCAA | TATGATAATC | 3200 |
| CGGGTGGAGA | GAATGACGCA | TTGGCAGAAA | ATGGTGGTGG | GTCTTTGCCA | 3250 |
| CCCAGTGCTA | ATATGCCTCC | ACAGAACATG | ATGCGTGCGT | CAAATCAAAT | 3300 |
| TGAAGCAGCA | CCTATGAATG | CCCCACCAAT | CAGTCAGCCA | GTTCCAAACA | 3350 |
| GGGCAAATAG | GAACTTGGA | CTTGATGGTG | ATGATATGGA | CATCCCGTGG | 3400 |
| TGTGATCTTA | ATATAAAGA | AAAGATTGGA | GCAGGTAATA | ATTTACGGA | 3450 |
| AAAATTAATG | ATTCGGTCTA | AAAATGCAAA | GAAATATGAA | ATTCTTGAGG | 3500 |
| AAGTGGTTTT | GCTTTGGACT | CTGTTCTCGA | ACAAATAAG | GAAAAGTGC | 3550 |
| CACCCATTTT | GAGATTACAT | TCTTCTCTGT | TGCCTTTAAT | TCTTCCACTC | 3600 |
| TAATTGAGC | GACTGCTCTT | TCAGGTTCCT | TTGGCACTGT | CCACCGTGCT | 3650 |
| GAGTGGCATG | GCTCGGTAAG | AACTTTTTTG | TCAGAATTTA | CGCAGCTGAA | 3700 |
| TTTTTTTTCG | CTCTAAAAAT | TTGGTTGTGA | CTTTTGGATC | TGCTTGGTAT | 3750 |
| TATAAAAGGC | AAAGTTATTG | TATATGTGAC | TCTCCGTTCT | GTCAGAAATT | 3800 |
| AAACACGGAC | AAAAGGTGTC | CCATTTTAGA | TGTATATGTG | TCTTTATATC | 3850 |
| ATAAATTTGT | CTTCCTGTTT | GAATTTTACA | ATTCTATCAC | TAGAAGAATT | 3900 |
| CTAATTTTGA | TTATTGCAGT | AATATTCTCT | ATCAATTTCA | GGATGTTGCT | 3950 |
| GTGAAAATTC | TCATGGAGCA | AGACTTCCAT | GCTGAGCGTG | TTAATGAGTT | 4000 |
| CTTAAGAGAG | GTGCACAAAT | AAAATTTCT | CTTGATTTTG | GTAATGAACT | 4050 |
| TGTTGTATTA | ATGTCTCCAA | TGATCTTGAT | TCGCTGTCAG | GTTGCGATAA | 4100 |
| TGAAACGCCT | TCGCCACCCT | AACATTGTTC | TCTTCATGGG | TGCGGTCACT | 4150 |
| CAACCTCCAA | ATTTGTCAAT | AGTGACAGAA | TATTTGTCAA | GGTACAATTA | 4200 |
| CTTGGATTTG | GAAGGTTTGA | TGTACTGAGT | GTAGAATTTT | GGCCTATAAT | 4250 |
| GACTCTAATA | CCATGATTTC | TTTCAAACAG | AGGTAGTTTA | TACAGACTTT | 4300 |
| TGCATAAAAG | TGGAGCAAGG | GAGCAATTAG | ATGAGAGACG | TCGCCTGAGT | 4350 |

```
ATGGCTTATG ATGTGGTATG TTTAACTCCT TATGTTACAT GTATGGGTGA       4400

TTACTTCCTG ATCTTGGTGT TTCTTCACAT GGAACTTTCT TTCCAATTCT       4450

CTGTCACAGG CTAAGGGAAT GAATTATCTT CACAATCGCA ATCCTCCAAT       4500

TGTGCATAGA GATCTAAAAT CTCCAAACTT ATTGGTTGAC AAAAAATATA       4550

CAGTCAAGGT TTGAATCTAA ATTAGAAATT GTTGTGTCCA ATGTTTTGAT       4600

TTTGATATTT TATTCCTCTT GTGAGACAAG CTTATATATA AATTATGATT       4650

TTTAATTCTA AATTGGTTTG GAGACATTAC AAAAAGGCGT TAATCTGCTG       4700

AAACTTAAAA GATACAGCAG CCTCAAGCTG TCGTCTTAAA AACAATCAGA       4750

ACATTATTAT TCTAACTCCT CAATTTGTCT TGAAATTTCA GGTTTGTGAT       4800

TTTGGTCTCT CGCGATTGAA GGCCAGCACG TTTCTTTCCT CGAAGTCAGC       4850

AGCTGGAACC GTAAGTTCAG TTTGTTTGAA ACTAAAACAC GCTGAACAAC       4900

GTAACTTTCT TCTAGGTCCT ATTTCCAATG GAAGCTAAAT AATTACTGAC       4950

TTTGATATAT CAGCCCGAGT GGATGGCACC AGAAGTCCTG CGAGATGAGC       5000

CGTCTAATGA AAAGTCAGAT GTGTACAGCT TCGGGGTCAT CTTGTGGGAG       5050

CTTGCTACAT TGCAACAACC ATGGGGTAAC TTAAATCCGG CTCAGGTACT       5100

TCCCACTCTA AACATCCCAA ATAATAATGA TATTATTTTG CATTTGGAAG       5150

TCCCTCACTC TACATTTCAT AACATGCTAT ATATGATCAT CCAACAAAAT       5200

GTTCCATAGG TTGTAGCTGC GGTTGGTTTC AAGTGTAAAC GGCTGGAGAT       5250

CCCGCGTAAT CTGAATCCTC AGGTTGCAGC CATAATCGAG GGTTGTTGGA       5300

CCAAGTACGT TAAGATTTTC TATCTCTTTT TTGAATTCTT CTTGAATAGA       5350

CTTCATGTTT ATGTATGTGT TTCATTACCA GTGAGCCATG GAAGCGTCCA       5400

TCATTTGCAA CTATAATGGA CTTGCTAAGA CCATTGATCA AATCAGCGGT       5450

TCCTCCGCCC AACCGCTCGG ATTTGTAAAA TACCCCCGGT CCATTCAAAA       5500

GTTGTTATAA TCATGATATG CACATATACT CTCAGCATTC TTTTGCTGCC       5550

CAGGAGGGAG ACACTAGTTA AGATATAGCT TTAAAGGTAC ATTCCTCATG       5600

AGCTATCAAT CATATCCTAC AGAATCCCAT GGTTTTTATA CATGTATTAT       5650

TTTTGCGATC TTTGTCTGCT GTTTTGTTCC CTTTTTAATG TTGCAGATTG       5700

TTAAAATGTA CATGACTATT GTCACAGGGA GGAAAAAAAA ATGTAGTAAT       5750

GGAAACAATG TGAGGGATAT AATCTATCTA TCTAGTCCCA AAGGGTAAGC       5800

AATATTGTGT TGTTATGTCT TTGTAGCAAT GCACTGAAAG CTATATTTAA       5850

TTACATTGCT GTACATTTAT ACCGCTAAAT TAGTTACTAA GCGAAGGTAA       5900

AAAAGAGCAG CTGGTAAATG CTGTCAAAGG GTTTTGCAAA CTCAATATGA       5950

TTCATTGGAT TTACATTTGT TCACTGTGCG ATTAGTCTGG ACTATAAACC       6000

AACAGAAATG AAATAAGACT GTAACTTTCG GAGACTCTAA TACAGATGAA       6050

TATAATCCCA AATCGTTAAA AACGCATTGG GACTGAAAAT ATCTAGATAC       6100

ATAGTCAACT ATTTTTGCCT TCGCGTCTAA GTAAGTTCCC ACACTTGAAA       6150

ACGACTTTAC CTGTCTTCCG AATTAATCGT TTGATGGATC GGTAACCAAT       6200

AGGATTGCGT AAATCAAAAT TATACAATAT TAAATTCTGA AAAAGGAAAC       6250

ACGAAAAGCG AATCAGTGAT TTGTGAGGGC CCAGTTCCAA ATTAGAAAGC       6300

TGACCTGGCA AA                                                6312
```

( 2 ) INFORMATION FOR SEQ ID NO:4:

( i ) SEQUENCE CHARACTERISTICS:
        ( A ) LENGTH: 6295 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
TATAGTCCAT  TCTCTCACTT  TCTATTCTAA  ATATTGTGGA  CGTTATAAAG       50
GCTTTTTATT  TATTTTATGT  CGAGTTTTTT  AGACTACGTA  GAGCCGAATG      100
AAAATTTCAT  GTTAGGTAT   ACGAAACTTG  GATCCAATGT  TACGGATTCA      150
GATTGGTGTA  AAAGATCAAA  TTTGATAGTA  TTTGGATTTG  ATAGGCAAGA      200
TGGTTTAGTA  TTTTACACTG  TGTATGTTCC  TCTTTTAGCT  TTGCGTTTTC      250
TACTTTCACT  ACGATACTAC  TTTTTATCTT  CCAATTTCAG  TTGCTTATCA      300
CCAAAATATG  AAATACCAAA  TTAATTGTTT  AAACAGTTTT  ATTAGCGATT      350
AAATTAGCAC  AAAACATATG  AATAGATATC  ATAGTCGAAT  ACAAAAATTA      400
GACAAATAAT  AATACACTAA  AAAACAAACT  AAATTGGAGA  ATTGTTTTGA      450
CAAAAAATAA  AAAAAATGTC  AAAGTTCCAT  AAAAAGGAGG  ACAAAAGAGG      500
AATATAACGA  AATTATCAAC  AGAAACGCAC  CGAGTAAGTT  TATTTCCTAT      550
GATAACGCAA  AAACAAAAAA  AAAATCCAAT  TCCATTAGAG  AGAGAGAGAG      600
AGAGAGAGAG  AGAGAGAGAC  TTTTTTAGAA  AGTACACAAA  AAAAATGAAA      650
AACTAGAGAG  AGAAACAAGT  GGCTAGCTAG  CTCGCCAAAC  TTCTTCAACA      700
ATGGCGGTTT  CCTAGGGTTT  GATGTTTATA  TGATCGGGAA  ACTCTCTCAT      750
CTAGATCGCG  ATAACTCTCT  TTTCCATGGA  AATGCCCGGT  AGAAGATCTA      800
ATTACACTTT  GCTTAGTCAA  TTTTCTGACG  ATCAGGTGTC  AGTTTCCGTC      850
ACCGGAGCTC  CTCCGCCTCA  CTATGATTCC  TTGTCGAGCG  AAAACAGGAG      900
CAACCATAAC  AGCGGGAACA  CCGGGAAAGC  TAAGGCGGAG  AGAGGCGGAT      950
TTGATTGGGA  TCCTAGCGGT  GGTGGTGGTG  GTGATCATAG  GTTGAATAAT     1000
CAACCGAATC  GGGTTGGGAA  TAATATGTAT  GCTTCGTCTC  TAGGGTTGCA     1050
AAGGCAATCC  AGTGGGAGTA  GTTTCGGTGA  GAGCTCTTTG  TCTGGGGATT     1100
ATTACATGCC  TACGCTTTCT  GCGGCGGCTA  ACGAGATCGA  ATCTGTTGGA     1150
TTTCCTCAAG  ATGATGGGTT  TAGGCTTGGA  TTTGGTGGTG  GTGGAGGAGA     1200
TTTGAGGATA  CAGATGGCGG  CGGACTCCGC  TGGAGGGTCT  TCATCTGGGA     1250
AGAGCTGGGC  GCAGCAGACG  GAGGAGAGTT  ATCAGCTGCA  GCTTGCATTG     1300
GCGTTAAGGC  TTTCGTCGGA  GGCTACTTGT  GCCGACGATC  CGAACTTTCT     1350
GGATCCTGTA  CCGGACGAGT  CTGCTTTACG  GACTTCGCCA  AGTTCAGCCG     1400
AAACCGTTTC  ACATCGTTTC  TGGGTATTTG  TTCCTGTTAA  GCTTTGTTTC     1450
CCAAAATTAT  TGAATCGTGG  TTATAGAGAT  ATGGTCCTCT  TGTTTCCGAA     1500
GTTTCAGTTA  GATCTCCTTA  CCAAAAGTCT  ATTAGTAGCA  AATGAGATAT     1550
GTTGTTTAGA  TACATTGCAG  AGTATGATTG  TTTTGTGTGC  TGCATCAGGT     1600
TAATGGCTGC  TTATCGTACT  ATGATAAAGT  TCCTGATGGG  TTTTATATGA     1650
TGAATGGTCT  GGATCCCTAT  ATTTGGACCT  TATGCATCGA  CCTGCATGAA     1700
```

| | | | | | |
|---|---|---|---|---|---|
| AGTGGTCGCA | TCCCTTCAAT | TGAATCATTA | AGAGCTGTTG | ATTCTGGTGT | 1750 |
| TGATTCTTCG | CTTGAAGCGA | TCATAGTTGA | TAGGCGTAGT | GATCCAGCCT | 1800 |
| TCAAGGAACT | TCACAATAGA | GTCCACGACA | TATCTTGTAG | CTGCATTACC | 1850 |
| ACAAAGAGG | TTGTTGATCA | GCTGGCAAAG | CTTATCTGCA | ATCGTATGGG | 1900 |
| GTTTGTACTC | ATACAATCCT | TACTATCCCT | TTGAACTTAT | ATTTTTATAT | 1950 |
| CTTCCTGTGA | TTTCTCACAT | TGTACTCGTT | AATTCTTGCT | TCCCCAGGGG | 2000 |
| TCCAGTTATC | ATGGGGAAG | ATGAGTTGGT | TCCCATGTGG | AAGGAGTGCA | 2050 |
| TTGATGGTCT | AAAAGAAATC | TTTAAAGTGG | TGGTTCCCAT | AGGTAGCCTC | 2100 |
| TCTGTTGGAC | TCTGCAGACA | TCGAGCTTTA | CTCTTCAAAG | TGAGATCCCA | 2150 |
| ACTTTGATGC | TATCCCCATG | ACATTAAGA | CATCTTGTGA | AATGATCATA | 2200 |
| TAAATTATTG | TGCTTCATCC | ATTGTTTTT | ATTGGAATAC | ATATGAAGAA | 2250 |
| CGTTGAATGT | GAAAAGTGGT | GTTATTGATT | AGAAAAAAT | AGGTTACTGA | 2300 |
| TAGTTGAATG | TTCCAAAGAA | AAAAAGTATT | TTATATCTTC | TATTTGGTGC | 2350 |
| ATGCAGGTAC | TGGCTGACAT | AATTGATTTA | CCCTGTCGAA | TTGCCAAAGG | 2400 |
| ATGTAAATAT | TGTAATAGAG | ACGATGCCGC | TTCGTGCCTT | GTCAGGTTTG | 2450 |
| GGCTTGATAG | GTATGATACA | AGTGATTGCG | AAAGAGCCTT | TATTTTCCTA | 2500 |
| TTTTCTTTGC | TTTTTGTTTC | TGGAAAAACA | ATTATAGCTC | CAAATGTTTC | 2550 |
| GCAGAATATT | AGGTTGATGA | CGTGGAAAAT | TTGTTTTGGT | TTCAGGGAGT | 2600 |
| ACCTGGTTGA | TTTAGTAGGA | AAGCCAGGTC | ACTTATGGGA | GCCTGATTCC | 2650 |
| TTGCTAAATG | GTCCTTCATC | TATCTCAATT | TCTTCTCCTC | TGCGGTTTCC | 2700 |
| ACGACCAAAG | CCAGTTGAAC | CCGCAGTCGA | TTTAGGTTA | CTAGCCAAAC | 2750 |
| AATATTTCTC | CGATAGCCAT | CGATCCTGCA | TCAGGTATTC | CCATACAAAA | 2800 |
| AACCTAAATA | ATATGTTAAC | TTTTTGCATG | CTGCTTACAT | CTCGTTTTGT | 2850 |
| ATTTCCCCTA | AAAGAGTAAT | CTCCTATCAT | TTAGGGTATT | TCTTGATCAT | 2900 |
| GTCTCAGTAT | CTGAAGTGTT | AGTAGTCTTA | GAATGATTCT | ATTGTTTGTT | 2950 |
| TTCTTGTCTC | TTTTCACTTT | AGTTGTTTTT | GGCTGTTGAT | GTGTATGTTT | 3000 |
| GTTGGTGGGT | TCTTTGCCTA | ATGATATTTA | AGGTTAAACT | TGTTAGTCTG | 3050 |
| CTGTTCAAGC | TTATGAATTC | TAGTGCATTT | ATGTGCAAGA | CTTGTCTTCT | 3100 |
| GGACTCTAAT | TTCTTATATC | TGCTTGTTTG | AATGGTTGTA | GATGATATGG | 3150 |
| GATTCTCAAT | GTTTCATAGG | CAATATGATA | ATCCGGGTGG | AGAGAATGAC | 3200 |
| GCATTGGCAG | AAAATGGTGG | TGGGTCTTTG | CCACCCAGTG | CTAATATGCC | 3250 |
| TCCACAGAAC | ATGATGCGTG | CGTCAAATCA | AATTGAAGCA | GCACCTATGA | 3300 |
| ATGCCCCACC | AATCAGTCAG | CCAGTTCCAA | ACAGGGCAAA | TAGGGAACTT | 3350 |
| GGACTTGATG | GTGATGATAT | GGACATCCCG | TGGTGTGATC | TTAATATAAA | 3400 |
| AGAAAAGATT | GGAGCAGGTA | ATAATTTTAC | GGAAAAATTA | ATGATTCGGT | 3450 |
| CTAAAAATGC | AAGAAATAT | GAATTCTTG | AGGAAGTGGT | TTTGCTTTGG | 3500 |
| ACTCTGTTCT | CGAACAAAAT | AAGGAAAAAG | TGCCACCCAT | TTGAGATTA | 3550 |
| CATTCTTCTC | TGTTGCCTTT | AATTCTTCCA | CTCTAATTTG | AGCGACTGCT | 3600 |
| CTTTCAGGTT | CCTTTGGCAC | TGTCCACCGT | GCTGAGTGGC | ATGGCTCGGT | 3650 |
| AAGAACTTTT | TTGTCAGAAT | TTACGCAGCT | GAATTTTTTT | TCGCTCTAAA | 3700 |

```
AATTTGGTTG  TGACTTTTGG  ATCTGCTTGG  TATTATAAAA  GGCAAAGTTA   3750
TTGTATATGT  GACTCTCCGT  TCTGTCAGAA  ATTAAACACG  GACAAAAGGT   3800
GTCCCATTTT  AGATGTATAT  GTGTCTTTAT  ATCATAAATT  TGTCTTCCTG   3850
TTTGAATTTT  ACAATTCTAT  CACTAGAAGA  ATTCTAATTT  TGATTATTGC   3900
AGTAATATTC  TCTATCAATT  TCAGGATGTT  GCTGTGAAAA  TTCTCATGGA   3950
GCAAGACTTC  CATGCTGAGC  GTGTTAATGA  GTTCTTAAGA  GAGGTGCACA   4000
AATAAAATTT  TCTCTTGATT  TTGGTAATGA  ACTTGTTGTA  TTAATGTCTC   4050
CAATGATCTT  GATTCGCTGT  CAGGTTGCGA  TAATGAAACG  CCTTCGCCAC   4100
CCTAACATTG  TTCTCTTCAT  GGGTGCGGTC  ACTCAACCTC  CAAATTTGTC   4150
AATAGTGACA  GAATATTTGT  CAAGGTACAA  TTACTTGGAT  TTGGAAGGTT   4200
TGATGTACTG  AGTGTAGAAT  TTTGGCCTAT  AATGACTCTA  ATACCATGAT   4250
TTCTTTCAAA  CAGAGGTAGT  TTATACAGAC  TTTTGCATAA  AAGTGGAGCA   4300
AGGGAGCAAT  TAGATGAGAG  ACGTCGCCTG  AGTATGGCTT  ATGATGTGGT   4350
ATGTTTAACT  CCTTATGTTA  CATGTATGGG  TGATTACTTC  CTGATCTTGG   4400
TGTTTCTTCA  CATGGAACTT  TCTTTCCAAT  TCTCTGTCAC  AGGCTAAGGG   4450
AATGAATTAT  CTTCACAATC  GCAATCCTCC  AATTGTGCAT  AGAGATCTAA   4500
AATCTCCAAA  CTTATTGGTT  GACAAAAAAT  ATACAGTCAA  GGTTTGAATC   4550
TAAATTAGAA  ATTGTTGTGT  CCAATGTTTT  GATTTGATA   TTTTATTCCT   4600
CTTGTGAGAC  AAGCTTATAT  ATAAATTATG  ATTTTTAATT  CTAAATTGGT   4650
TTGGAGACAT  TACAAAAAGG  CGTTAATCTG  CTGAAACTTA  AAAGATACAG   4700
CAGCCTCAAG  CTGTCGTCTT  AAAAACAATC  AGAACATTAT  TATTCTAACT   4750
CCTCAATTTG  TCTTGAAATT  TCAGGTTTGT  GATTTTGGTC  TCTCGCGATT   4800
GAAGGCCAGC  ACGTTTCTTT  CCTCGAAGTC  AGCAGCTGGA  ACCGTAAGTT   4850
CAGTTTGTTT  GAAACTAAAA  CACGCTGAAC  AACGTAACTT  TCTTCTAGGT   4900
CCTATTTCCA  ATGGAAGCTA  AATAATTACT  GACTTTGATA  TATCAGCCCG   4950
AGTGGATGGC  ACCAGAAGTC  CTGCGAGATG  AGCCGTCTAA  TGAAAAGTCA   5000
GATGTGTACA  GCTTCGGGGT  CATCTTGTGG  GAGCTTGCTA  CATTGCAACA   5050
ACCATGGGGT  AACTTAAATC  CGGCTCAGGT  ACTTCCCACT  CTAAACATCC   5100
CAAATAATAA  TGATATTATT  TTGCATTTGG  AAGTCCCTCA  CTCTACATTT   5150
CATAACATGC  TATATATGAT  CATCCAACAA  AATGTTCCAT  AGGTTGTAGC   5200
TGCGGTTGGT  TTCAAGTGTA  AACGGCTGGA  GATCCGCGT   AATCTGAATC   5250
CTCAGGTTGC  AGCCATAATC  GAGGGTTGTT  GGACCAAGTA  CGTTAAGATT   5300
TTCTATCTCT  TTTTTGAATT  CTTCTTGAAT  AGACTTCATG  TTTATGTATG   5350
TGTTTCATTA  CCAGTGAGCC  ATGGAAGCGT  CCATCATTTG  CAACTATAAT   5400
GGACTTGCTA  AGACCATTGA  TCAAATCAGC  GGTTCCTCCG  CCCAACCGCT   5450
CGGATTTGTA  AAATACCCCC  GGTCCATTCA  AAAGTTGTTA  TAATCATGAT   5500
ATGCACATAT  ACTCTCAGCA  TTCTTTTGCT  GCCCAGGAGG  GAGACACTAG   5550
TTAAGATATA  GCTTAAAGG   TACATTCCTC  ATGAGCTATC  AATCATATCC   5600
TACAGAATCC  CATGGTTTTT  ATACATGTAT  TATTTTTGCG  ATCTTTGTCT   5650
GCTGTTTTGT  TCCCTTTTTA  ATGTTGCAGA  TTGTTAAAAT  GTACATGACT   5700
```

| | | | | | |
|---|---|---|---|---|---|
| ATTGTCACAG | GGAGGAAAAA | AAAATGTAGT | AATGGAAACA | ATGTGAGGGA | 5750 |
| TATAATCTAT | CTATCTAGTC | CCAAAGGGTA | AGCAATATTG | TGTTGTTATG | 5800 |
| TCTTTGTAGC | AATGCACTGA | AAGCTATATT | TAATTACATT | GCTGTACATT | 5850 |
| TATACCGCTA | AATTAGTTAC | TAAGCGAAGG | TAAAAAGAG | CAGCTGGTAA | 5900 |
| ATGCTGTCAA | AGGGTTTTGC | AAACTCAATA | TGATTCATTG | GATTTACATT | 5950 |
| TGTTCACTGT | GCGATTAGTC | TGGACTATAA | ACCAACAGAA | ATGAAATAAG | 6000 |
| ACTGTAACTT | TCGGAGACTC | TAATACAGAT | GAATATAATC | CCAAATCGTT | 6050 |
| AAAAACGCAT | TGGGACTGAA | AATATCTAGA | TACATAGTCA | ACTATTTTG | 6100 |
| CCTTCGCGTC | TAAGTAAGTT | CCCACACTTG | AAAACGACTT | TACCTGTCTT | 6150 |
| CCGAATTAAT | CGTTTGATGG | ATCGGTAACC | AATAGGATTG | CGTAAATCAA | 6200 |
| AATTATACAA | TATTAAATTC | TGAAAAAGGA | AACACGAAAA | GCGAATCAGT | 6250 |
| GATTGTGAG | GGCCCAGTTC | CAAATTAGAA | AGCTGACCTG | GCAAA | 6295 |

(2) INFORMATION FOR SEQ ID NO:5:

(i) SEQUENCE CHARACTERISTICS:
        (A) LENGTH: 6312 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

| | | | | | |
|---|---|---|---|---|---|
| TATAGTCCAT | TCTCTCACTT | TCTATTCTAA | ATATTGTGGA | CGTTATAAAG | 50 |
| GCTTTTTATT | TATTTTATGT | CGAGTTTTTT | AGACTACGTA | GAGCCGAATG | 100 |
| AAAATTTCAT | GTTAGGTAT | ACGAAACTTG | GATCCAATGT | TACGGATTCA | 150 |
| GATTGGTGTA | AAAGATCAAA | TTTGATAGTA | TTTGGATTTG | ATAGGCAAGA | 200 |
| TGGTTTAGTA | TTTTACACTG | TGTATGTTCC | TCTTTTAGCT | TTGCGTTTTC | 250 |
| TACTTTCACT | ACGATACTAC | TTTTTATCTT | CCAATTTCAG | TTGCTTATCA | 300 |
| CCAAAATATG | AAATACCAAA | TTAATTGTTT | AAACAGTTTT | ATTAGCGATT | 350 |
| AAATTAGCAC | AAAACATATG | AATAGATATC | ATAGTCGAAT | ACAAAAATTA | 400 |
| GACAAATAAT | AATACACTAA | AAAACAAACT | AAATTGGAGA | ATTGTTTTGA | 450 |
| CAAAAAATAA | AAAAAATGTC | AAAGTTCCAT | AAAAAGGAGG | ACAAAGAGG | 500 |
| AATATAACGA | AATTATCAAC | AGAAACGCAC | CGAGTAAGTT | TATTTCCTAT | 550 |
| GATAACGCAA | AAACAAAAAA | AAATCCAAT | TCCATTAGAG | AGAGAGAGAG | 600 |
| AGAGAGAGAG | AGAGAGAGAC | TTTTTAGAA | AGTACACAAA | AAAATGAAA | 650 |
| AACTAGAGAG | AGAAACAAGT | GGCTAGCTAG | CTCGCCAAAC | TTCTTCAACA | 700 |
| ATGGCGGTTT | CCTAGGGTTT | GATGTTTATA | TGATCGGGAA | ACTCTCTCAT | 750 |
| CTAGATCGCG | ATAACTCTCT | TTTCCATGGA | AATGCCCGGT | AGAAGATCTA | 800 |
| ATTACACTTT | GCTTAGTCAA | TTTTCTGACG | ATCAGGTGTC | AGTTTCCGTC | 850 |
| ACCGGAGCTC | CTCCGCCTCA | CTATGATTCC | TTGTCGAGCG | AAAACAGGAG | 900 |
| CAACCATAAC | AGCGGGAACA | CCGGGAAAGC | TAAGGCGGAG | AGAGGCGGAT | 950 |
| TTGATTGGGA | TCCTAGCGGT | GGTGGTGGTG | GTGATCATAG | GTTGAATAAT | 1000 |
| CAACCGAATC | GGGTTGGGAA | TAATATGTAT | GCTTCGTCTC | TAGGGTTGCA | 1050 |

| | | | | | |
|---|---|---|---|---|---|
| AAGGCAATCC | AGTGGGAGTA | GTTTCGGTGA | GAGCTCTTTG | TCTGGGGATT | 1100 |
| ATTACATGCC | TACGCTTTCT | GCGGCGGCTA | ACGAGATCGA | ATCTGTTGGA | 1150 |
| TTTCCTCAAG | ATGATGGGTT | TAGGCTTGGA | TTTGGTGGTG | GTGGAGGAGA | 1200 |
| TTTGAGGATA | CAGATGGCGG | CGGACTCCGC | TGGAGGGTCT | TCATCTGGGA | 1250 |
| AGAGCTGGGC | GCAGCAGACG | GAGGAGAGTT | ATCAGCTGCA | GCTTGCATTG | 1300 |
| GCGTTAAGGC | TTTCGTCGGA | GGCTACTTGT | GCCGACGATC | CGAACTTTCT | 1350 |
| GGATCCTGTA | CCGGACGAGT | CTGCTTTACG | GACTTCGCCA | AGTTCAGCCG | 1400 |
| AAACCGTTTC | ACATCGTTTC | TGGGTATTTG | TTCCTGTTAA | GCTTTGTTTC | 1450 |
| CCAAAATTAT | TGAATCGTGG | TTATAGAGAT | ATGGTCCTCT | TGTTTCCGAA | 1500 |
| GTTTCAGTTA | GATCTCCTTA | CCAAAAGTCT | ATTAGTAGCA | AATGAGATAT | 1550 |
| GTTGTTTAGA | TACATTGCAG | AGTATGATTG | TTTTGTGTGC | TGCATCAGGT | 1600 |
| TAATGGCTGC | TTATCGTACT | ATGATAAAGT | TCCTGATGGG | TTTTATATGA | 1650 |
| TGAATGGTCT | GGATCCCTAT | ATTTGGACCT | TATGCATCGA | CCTGCATGAA | 1700 |
| AGTGGTCGCA | TCCCTTCAAT | TGAATCATTA | AGAGCTGTTG | ATTCTGGTGT | 1750 |
| TGATTCTTCG | CTTGAAGCGA | TCATAGTTGA | TAGGCGTAGT | GATCCAGCCT | 1800 |
| TCAAGGAACT | TCACAATAGA | GTCCACGACA | TATCTTGTAG | CTGCATTACC | 1850 |
| ACAAAGAGG | TTGTTGATCA | GCTGGCAAAG | CTTATCTGCA | ATCGTATGGG | 1900 |
| GTTGTACTC | ATACAATCCT | TACTATCCCT | TTGAACTTAT | ATTTTATAT | 1950 |
| CTTCCTGTGA | TTTCTCACAT | TGTACTCGTT | AATTCTTGCT | TCCCCAGGGG | 2000 |
| TCCAGTTATC | ATGGGGGAAG | ATGAGTTGGT | TCCCATGTGG | AAGGAGTGCA | 2050 |
| TTGATGGTCT | AAAAGAAATC | TTTAAAGTGG | TGGTTCCCAT | AGGTAGCCTC | 2100 |
| TCTGTTGGAC | TCTGCAGACA | TCGAGCTTTA | CTCTTCAAAG | TGAGATCCCA | 2150 |
| ACTTTGATGC | TATCCCCATG | ACATTAAGA | CATCTTGTGA | AATGATCATA | 2200 |
| TAAATTATTG | TGCTTCATCC | ATTTGTTTTT | ATTGGAATAC | ATATGAAGAA | 2250 |
| CGTTGAATGT | GAAAAGTGGT | GTTATTGATT | AGAAAAAAAT | AGGTTACTGA | 2300 |
| TAGTTGAATG | TTCCAAAGAA | AAAAGTATT | TTATATCTTC | TATTTGGTGC | 2350 |
| ATGCAGGTAC | TGGCTGACAT | AATTGATTTA | CCCTGTCGAA | TTGCCAAAGG | 2400 |
| ATGTAAATAT | TGTAATAGAG | ACGATGCCGC | TTCGTGCCTT | GTCAGGTTTG | 2450 |
| GGCTTGATAG | GTATGATACA | AGTGATTGCG | AAAGAGCCTT | TATTTTCCTA | 2500 |
| TTTTCTTTGC | TTTTTGTTTC | TGGAAAAACA | ATTATAGCTC | CAAATGTTTC | 2550 |
| GCAGAATATT | AGGTTGATGA | CGTGGAAAAT | TTGTTTTGGT | TTCAGGGAGT | 2600 |
| ACCTGGTTGA | TTTAGTAGGA | AAGCCAGGTC | ACTTATGGGA | GCCTGATTCC | 2650 |
| TTGCTAAATG | GTCCTTCATC | TATCTCAATT | TCTTCTCCTC | TGCGGTTTCC | 2700 |
| ATGACCAAAG | CCAGTTGAAC | CCGCAGTCGA | TTTAGGTTA | CTAGCCAAAC | 2750 |
| AATATTTCTC | CGATAGCCAG | TCTCTTAATC | TTGTTTTCGA | TCCTGCATCA | 2800 |
| GGTATTCCCA | TACAAAAAAC | CTAAATAATA | TGTTAACTTT | TTGCATGCTG | 2850 |
| CTTACATCTC | GTTTTGTATT | TCCCCTAAAA | GAGTAATCTC | CTATCATTTA | 2900 |
| GGGTATTTCT | TGATCATGTC | TCAGTATCTG | AAGTGTTAGT | AGTCTTAGAA | 2950 |
| TGATTCTATT | GTTTGTTTTC | TTGTCTCTTT | TCACTTTAGT | TGTTTTGGC | 3000 |
| TGTTGATGTG | TATGTTTGTT | GGTGGGTTCT | TTGCCTAATG | ATATTTAAGG | 3050 |

```
TTAAACTTGT TAGTCTGCTG TTCAAGCTTA TGAATTCTAG TGCATTTATG    3100
TGCAAGACTT GTCTTCTGGA CTCTAATTTC TTATATCTGC TTGTTTGAAT    3150
GGTTGTAGAT GATATGGGAT TCTCAATGTT TCATAGGCAA TATGATAATC    3200
CGGGTGGAGA GAATGACGCA TTGGCAGAAA ATGGTGGTGG GTCTTTGCCA    3250
CCCAGTGCTA ATATGCCTCC ACAGAACATG ATGCGTGCGT CAAATCAAAT    3300
TGAAGCAGCA CCTATGAATG CCCCACCAAT CAGTCAGCCA GTTCCAAACA    3350
GGGCAAATAG GAACTTGGA CTTGATGGTG ATGATATGGA CATCCCGTGG    3400
TGTGATCTTA ATATAAAGA AAGATTGGA GCAGGTAATA ATTTTACGGA      3450
AAAATTAATG ATTCGGTCTA AAAATGCAAA GAAATATGAA ATTCTTGAGG    3500
AAGTGGTTTT GCTTTGGACT CTGTTCTCGA ACAAATAAG GAAAAAGTGC     3550
CACCCATTTT GAGATTACAT TCTTCTCTGT TGCCTTTAAT TCTTCCACTC    3600
TAATTTGAGC GACTGCTCTT TCAGGTTCCT TTGGCACTGT CCACCGTGCT    3650
GAGTGGCATG GCTCGGTAAG AACTTTTTG TCAGAATTTA CGCAGCTGAA     3700
TTTTTTTTCG CTCTAAAAAT TTGGTTGTGA CTTTTGGATC TGCTTGGTAT    3750
TATAAAGGC AAAGTTATTG TATATGTGAC TCTCCGTTCT GTCAGAAATT     3800
AAACACGGAC AAAAGGTGTC CCATTTAGA TGTATATGTG TCTTTATATC     3850
ATAAATTTGT CTTCCTGTTT GAATTTTACA ATTCTATCAC TAGAAGAATT    3900
CTAATTTGA TTATTGCAGT AATATTCTCT ATCAATTTCA GGATGTTGCT     3950
GTGAAAATTC TCATGGAGCA AGACTTCCAT GCTGAGCGTG TTAATGAGTT    4000
CTTAAGAGAG GTGCACAAAT AAAATTTCT CTTGATTTTG GTAATGAACT     4050
TGTTGTATTA ATGTCTCCAA TGATCTTGAT TCGCTGTCAG GTTGCGATAA    4100
TGAAACGCCT TCGCCACCCT AACATTGTTC TCTTCATGGG TGCGGTCACT    4150
CAACCTCCAA ATTTGTCAAT AGTGACAGAA TATTTGTCAA GGTACAATTA    4200
CTTGGATTTG GAAGGTTTGA TGTACTGAGT GTAGAATTTT GGCCTATAAT    4250
GACTCTAATA CCATGATTTC TTTCAAACAG AGGTAGTTTA TACAGACTTT    4300
TGCATAAAAG TGGAGCAAGG GAGCAATTAG ATGAGAGACG TCGCCTGAGT    4350
ATGGCTTATG ATGTGGTATG TTTAACTCCT TATGTTACAT GTATGGGTGA    4400
TTACTTCCTG ATCTTGGTGT TTCTTCACAT GGAACTTTCT TTCCAATTCT    4450
CTGTCACAGG CTAAGGGAAT GAATTATCTT CACAATCGCA ATCCTCCAAT    4500
TGTGCATAGA GATCTAAAAT CTCCAAACTT ATTGGTTGAC AAAAAATATA    4550
CAGTCAAGGT TTGAATCTAA ATTAGAAATT GTTGTGTCCA ATGTTTTGAT    4600
TTTGATATTT TATTCCTCTT GTGAGACAAG CTTATATATA AATTATGATT    4650
TTTAATTCTA AATTGGTTTG GAGACATTAC AAAAAGGCGT TAATCTGCTG    4700
AAACTTAAAA GATACAGCAG CCTCAAGCTG TCGTCTTAAA AACAATCAGA    4750
ACATTATTAT TCTAACTCCT CAATTGTCT TGAAATTTCA GGTTTGTGAT     4800
TTTGGTCTCT CGCGATTGAA GGCCAGCACG TTTCTTTCCT CGAAGTCAGC    4850
AGCTGGAACC GTAAGTTCAG TTTGTTGAA ACTAAAACAC GCTGAACAAC     4900
GTAACTTTCT TCTAGGTCCT ATTTCCAATG GAAGCTAAAT AATTACTGAC    4950
TTTGATATAT CAGCCCGAGT GGATGGCACC AGAAGTCCTG CGAGATGAGC    5000
CGTCTAATGA AAAGTCAGAT GTGTACAGCT TCGGGGTCAT CTTGTGGGAG    5050
```

| | | | | | |
|---|---|---|---|---|---|
| CTTGCTACAT | TGCAACAACC | ATGGGGTAAC | TTAAATCCGG | CTCAGGTACT | 5100 |
| TCCCACTCTA | AACATCCCAA | ATAATAATGA | TATTATTTTG | CATTTGGAAG | 5150 |
| TCCCTCACTC | TACATTTCAT | AACATGCTAT | ATATGATCAT | CCAACAAAAT | 5200 |
| GTTCCATAGG | TTGTAGCTGC | GGTTGGTTTC | AAGTGTAAAC | GGCTGGAGAT | 5250 |
| CCCGCGTAAT | CTGAATCCTC | AGGTTGCAGC | CATAATCGAG | GGTTGTTGGA | 5300 |
| CCAAGTACGT | TAAGATTTTC | TATCTCTTTT | TTGAATTCTT | CTTGAATAGA | 5350 |
| CTTCATGTTT | ATGTATGTGT | TTCATTACCA | GTGAGCCATG | GAAGCGTCCA | 5400 |
| TCATTTGCAA | CTATAATGGA | CTTGCTAAGA | CCATTGATCA | AATCAGCGGT | 5450 |
| TCCTCCGCCC | AACCGCTCGG | ATTTGTAAAA | TACCCCGGT | CCATTCAAAA | 5500 |
| GTTGTTATAA | TCATGATATG | CACATATACT | CTCAGCATTC | TTTTGCTGCC | 5550 |
| CAGGAGGGAG | ACACTAGTTA | AGATATAGCT | TTAAAGGTAC | ATTCCTCATG | 5600 |
| AGCTATCAAT | CATATCCTAC | AGAATCCCAT | GGTTTTTATA | CATGTATTAT | 5650 |
| TTTTGCGATC | TTTGTCTGCTG | TTTTGTTCC | CTTTTAATG | TTGCAGATTG | 5700 |
| TTAAAATGTA | CATGACTATT | GTCACAGGGA | GGAAAAAAA | ATGTAGTAAT | 5750 |
| GGAAACAATG | TGAGGGATAT | AATCTATCTA | TCTAGTCCCA | AAGGGTAAGC | 5800 |
| AATATTGTGT | TGTTATGTCT | TTGTAGCAAT | GCACTGAAAG | CTATATTTAA | 5850 |
| TTACATTGCT | GTACATTTAT | ACCGCTAAAT | TAGTTACTAA | GCGAAGGTAA | 5900 |
| AAAAGAGCAG | CTGGTAAATG | CTGTCAAAGG | GTTTTGCAAA | CTCAATATGA | 5950 |
| TTCATTGGAT | TTACATTTGT | TCACTGTGCG | ATTAGTCTGG | ACTATAAACC | 6000 |
| AACAGAAATG | AAATAAGACT | GTAACTTTCG | GAGACTCTAA | TACAGATGAA | 6050 |
| TATAATCCCA | AATCGTTAAA | AACGCATTGG | GACTGAAAAT | ATCTAGATAC | 6100 |
| ATAGTCAACT | ATTTTTGCCT | TCGCGTCTAA | GTAAGTTCCC | ACACTTGAAA | 6150 |
| ACGACTTTAC | CTGTCTTCCG | AATTAATCGT | TTGATGGATC | GGTAACCAAT | 6200 |
| AGGATTGCGT | AAATCAAAAT | TATACAATAT | TAAATTCTGA | AAAAGGAAAC | 6250 |
| ACGAAAAGCG | AATCAGTGAT | TTGTGAGGGC | CCAGTTCCAA | ATTAGAAAGC | 6300 |
| TGACCTGGCA | AA | | | | 6312 |

( 2 ) INFORMATION FOR SEQ ID NO:6:

( i ) SEQUENCE CHARACTERISTICS:
        ( A ) LENGTH: 6312 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

| | | | | | |
|---|---|---|---|---|---|
| TATAGTCCAT | TCTCTCACTT | TCTATTCTAA | ATATTGTGGA | CGTTATAAAG | 50 |
| GCTTTTTATT | TATTTTATGT | CGAGTTTTTT | AGACTACGTA | GAGCCGAATG | 100 |
| AAAATTTCAT | GTTTAGGTAT | ACGAAACTTG | GATCCAATGT | TACGGATTCA | 150 |
| GATTGGTGTA | AAAGATCAAA | TTTGATAGTA | TTTGGATTTG | ATAGGCAAGA | 200 |
| TGGTTTAGTA | TTTTACACTG | TGTATGTTCC | TCTTTTAGCT | TTGCGTTTTC | 250 |
| TACTTTCACT | ACGATACTAC | TTTTTATCTT | CCAATTTCAG | TTGCTTATCA | 300 |
| CCAAAATATG | AAATACCAAA | TTAATTGTTT | AAACAGTTTT | ATTAGCGATT | 350 |
| AAATTAGCAC | AAAACATATG | AATAGATATC | ATAGTCGAAT | ACAAAAATTA | 400 |

| | | | | | |
|---|---|---|---|---|---|
| GACAAATAAT | AATACACTAA | AAAACAAACT | AAATTGGAGA | ATTGTTTTGA | 450 |
| CAAAAAATAA | AAAAAATGTC | AAAGTTCCAT | AAAAAGGAGG | ACAAAGAGG | 500 |
| AATATAACGA | AATTATCAAC | AGAAACGCAC | CGAGTAAGTT | TATTTCCTAT | 550 |
| GATAACGCAA | AAACAAAAAA | AAAATCCAAT | TCCATTAGAG | AGAGAGAGAG | 600 |
| AGAGAGAGAG | AGAGAGAGAC | TTTTTTAGAA | AGTACACAAA | AAAAATGAAA | 650 |
| AACTAGAGAG | AGAAACAAGT | GGCTAGCTAG | CTCGCCAAAC | TTCTTCAACA | 700 |
| ATGGCGGTTT | CCTAGGGTTT | GATGTTTATA | TGATCGGGAA | ACTCTCTCAT | 750 |
| CTAGATCGCG | ATAACTCTCT | TTTCCATGGA | AATGCCCGGT | AGAAGATCTA | 800 |
| ATTACACTTT | GCTTAGTCAA | TTTTCTGACG | ATCAGGTGTC | AGTTTCCGTC | 850 |
| ACCGGAGCTC | CTCCGCCTCA | CTATGATTCC | TTGTCGAGCG | AAAACAGGAG | 900 |
| CAACCATAAC | AGCGGGAACA | CCGGGAAAGC | TAAGGCGGAG | AGAGGCGGAT | 950 |
| TTGATTGGGA | TCCTAGCGGT | GGTGGTGGTG | GTGATCATAG | GTTGAATAAT | 1000 |
| CAACCGAATC | GGGTTGGGAA | TAATATGTAT | GCTTCGTCTC | TAGGGTTGCA | 1050 |
| AAGGCAATCC | AGTGGGAGTA | GTTTCGGTGA | GAGCTCTTTG | TCTGGGGATT | 1100 |
| ATTACATGCC | TACGCTTTCT | GCGGCGGCTA | ACGAGATCGA | ATCTGTTGGA | 1150 |
| TTTCCTCAAG | ATGATGGGTT | TAGGCTTGGA | TTTGGTGGTG | GTGGAGGAGA | 1200 |
| TTTGAGGATA | CAGATGGCGG | CGGACTCCGC | TGGAGGGTCT | TCATCTGGGA | 1250 |
| AGAGCTGGGC | GCAGCAGACG | GAGGAGAGTT | ATCAGCTGCA | GCTTGCATTG | 1300 |
| GCGTTAAGGC | TTTCGTCGGA | GGCTACTTGT | GCCGACGATC | CGAACTTTCT | 1350 |
| GGATCCTGTA | CCGGACGAGT | CTGCTTTACG | GACTTCGCCA | AGTTCAGCCG | 1400 |
| AAACCGTTTC | ACATCGTTTC | TGGGTATTTG | TTCCTGTTAA | GCTTTGTTTC | 1450 |
| CCAAAATTAT | TGAATCGTGG | TTATAGAGAT | ATGGTCCTCT | TGTTTCCGAA | 1500 |
| GTTTCAGTTA | GATCTCCTTA | CCAAAAGTCT | ATTAGTAGCA | AATGAGATAT | 1550 |
| GTTGTTTAGA | TACATTGCAG | AGTATGATTG | TTTTGTGTGC | TGCATCAGGT | 1600 |
| TAATGGCTGC | TTATCGTACT | ATGATAAAGT | TCCTGATGGG | TTTTATATGA | 1650 |
| TGAATGGTCT | GGATCCCTAT | ATTTGGACCT | TATGCATCGA | CCTGCATGAA | 1700 |
| AGTGGTCGCA | TCCCTTCAAT | TGAATCATTA | AGAGCTGTTG | ATTCTGGTGT | 1750 |
| TGATTCTTCG | CTTGAAGCGA | TCATAGTTGA | TAGGCGTAGT | GATCCAGCCT | 1800 |
| TCAAGGAACT | TCACAATAGA | GTCCACGACA | TATCTTGTAG | CTGCATTACC | 1850 |
| ACAAAGAGG | TTGTTGATCA | GCTGGCAAAG | CTTATCTGCA | ATCGTATGGG | 1900 |
| GTTTGTACTC | ATACAATCCT | TACTATCCCT | TGAACTTAT | ATTTTTATAT | 1950 |
| CTTCCTGTGA | TTTCTCACAT | TGTACTCGTT | AATTCTTGCT | TCCCCAGGGG | 2000 |
| TCCAGTTATC | ATGGGGAAG | ATGAGTTGGT | TCCCATGTGG | AAGGAGTGCA | 2050 |
| TTGATGGTCT | AAAAGAAATC | TTTAAAGTGG | TGGTTCCCAT | AGGTAGCCTC | 2100 |
| TCTGTTGGAC | TCTGCAGACA | TCGAGCTTTA | CTCTTCAAAG | TGAGATCCCA | 2150 |
| ACTTTGATGC | TATCCCCATG | ACATTAAGA | CATCTTGTGA | AATGATCATA | 2200 |
| TAAATTATTG | TGCTTCATCC | ATTTGTTTTT | ATTGGAATAC | ATATGAAGAA | 2250 |
| CGTTGAATGT | GAAAAGTGGT | GTTATTGATT | AGAAAAAAAT | AGGTTACTGA | 2300 |
| TAGTTGAATG | TTCCAAAGAA | AAAAAGTATT | TTATATCTTC | TATTTGGTGC | 2350 |
| ATGCAGGTAC | TGGCTGACAT | AATTGATTTA | CCCTGTCGAA | TTGCCAAAGG | 2400 |

```
ATGTAAATAT TGTAATAGAG ACGATGCCGC TTCGTGCCTT GTCAGGTTTG      2450
GGCTTGATAG GTATGATACA AGTGATTGCG AAAGAGCCTT TATTTTCCTA      2500
TTTTCTTTGC TTTTTGTTTC TGGAAAAACA ATTATAGCTC CAAATGTTTC      2550
GCAGAATATT AGGTTGATGA CGTGGAAAAT TTGTTTTGGT TTCAGGGAGT      2600
ACCTGGTTGA TTTAGTAGGA AAGCCAGGTC ACTTATGGGA GCCTGATTCC      2650
TTGCTAAATG GTCCTTCATC TATCTCAATT TCTTCTCCTC TGCGGTTTCC      2700
ACGACCAAAG CCAGTTGAAC CCGCAGTCGA TTTAGGTTA CTAGCCAAAC       2750
AATATTTCTC CGATAGCCAG TCTCTTAATC TTGTTTTCGA TCCTGCATCA      2800
GGTATTCCCA TACAAAAAAC CTAAATAATA TGTTAACTTT TGCATGCTG       2850
CTTACATCTC GTTTTGTATT TCCCCTAAAA GAGTAATCTC CTATCATTTA      2900
GGGTATTTCT TGATCATGTC TCAGTATCTG AAGTGTTAGT AGTCTTAGAA      2950
TGATTCTATT GTTTGTTTTC TTGTCTCTTT TCACTTTAGT TGTTTTTGGC      3000
TGTTGATGTG TATGTTTGTT GGTGGGTTCT TTGCCTAATG ATATTTAAGG      3050
TTAAACTTGT TAGTCTGCTG TTCAAGCTTA TGAATTCTAG TGCATTTATG      3100
TGCAAGACTT GTCTTCTGGA CTCTAATTTC TTATATCTGC TTGTTTGAAT      3150
GGTTGTAGAT GATATGGGAT TCTCAATGTT TCATAGGCAA TATGATAATC      3200
CGGGTGGAGA GAATGACGCA TTGGCAGAAA ATGGTGGTGG GTCTTTGCCA      3250
CCCAGTGCTA ATATGCCTCC ACAGAACATG ATGCGTGCGT CAAATCAAAT      3300
TGAAGCAGCA CCTATGAATG CCCCACCAAT CAGTCAGCCA GTTCCAAACA      3350
GGGCAAATAG GGAACTTGGA CTTGATGGTG ATGATATGGA CATCCCGTGG      3400
TGTGATCTTA ATATAAAAGA AAAGATTGGA GCAGGTAATA ATTTTACGGA      3450
AAAATTAATG ATTCGGTCTA AAAATGCAAA GAAATATGAA ATTCTTGAGG      3500
AAGTGGTTTT GCTTTGGACT CTGTTCTCGA ACAAAATAAG GAAAAGTGC      3550
CACCCATTTT GAGATTACAT TCTTCTCTGT TGCCTTTAAT TCTTCCACTC      3600
TAATTTGAGC GACTGCTCTT TCAGGTTCCT TTGGCACTGT CCACCGTGCT      3650
GAGTGGCATG GCTCGGTAAG AACTTTTTG TCAGAATTTA CGCAGCTGAA       3700
TTTTTTTTCG CTCTAAAAAT TTGGTTGTGA CTTTTGGATC TGCTTGGTAT      3750
TATAAAAGGC AAAGTTATTG TATATGTGAC TCTCCGTTCT GTCAGAAATT      3800
AAACACGGAC AAAAGGTGTC CCATTTTAGA TGTATATGTG TCTTTATATC      3850
ATAAATTTGT CTTCCTGTTT GAATTTTACA ATTCTATCAC TAGAAGAATT      3900
CTAATTTTGA TTATTGCAGT AATATTCTCT ATCAATTTCA GGATGTTGCT      3950
GTGAAAATTC TCATGGAGCA AGACTTCCAT GCTGAGCGTG TTAATGAGTT      4000
CTTAAGAGAG GTGCACAAAT AAAATTTCT CTTGATTTG GTAATGAACT        4050
TGTTGTATTA ATGTCTCCAA TGATCTTGAT TCGCTGTCAG GTTGCGATAA      4100
TGAAACGCCT TCGCCACCCT AACATTGTTC TCTTCATGGG TGCGGTCACT      4150
CAACCTCCAA ATTTGTCAAT AGTGACAGAA TATTTGTCAA GGTACAATTA      4200
CTTGGATTTG GAAGGTTTGA TGTACTGAGT GTAGAATTTT GGCCTATAAT      4250
GACTCTAATA CCATGATTTC TTTCAAACAG AGGTAGTTTA TACAGACTTT      4300
TGCATAAAAG TGGAGCAAGG GAGCAATTAG ATGAGAGACG TCGCCTGAGT      4350
ATGGCTTATG ATGTGGTATG TTTAACTCCT TATGTTACAT GTATGGGTGA      4400
```

```
TTACTTCCTG ATCTTGGTGT TTCTTCACAT GGAACTTTCT TTCCAATTCT        4450
CTGTCACAGG CTAAGGGAAT GAATTATCTT CACAATCGCA ATCCTCCAAT        4500
TGTGCATAGA GATCTAAAAT CTCCAAACTT ATTGGTTGAC AAAAAATATA        4550
CAGTCAAGGT TTGAATCTAA ATTAGAAATT GTTGTGTCCA ATGTTTTGAT        4600
TTTGATATTT TATTCCTCTT GTGAGACAAG CTTATATATA AATTATGATT        4650
TTTAATTCTA AATTGGTTTG GAGACATTAC AAAAAGGCGT TAATCTGCTG        4700
AAACTTAAAA GATACAGCAG CCTCAAGCTG TCGTCTTAAA AACAATCAGA        4750
ACATTATTAT TCTAACTCCT CAATTGTCT TGAAATTTCA GGTTTGTGAA         4800
TTTGGTCTCT CGCGATTGAA GGCCAGCACG TTTCTTTCCT CGAAGTCAGC        4850
AGCTGGAACC GTAAGTTCAG TTTGTTTGAA ACTAAACAC GCTGAACAAC         4900
GTAACTTTCT TCTAGGTCCT ATTTCCAATG GAAGCTAAAT AATTACTGAC        4950
TTTGATATAT CAGCCCGAGT GGATGGCACC AGAAGTCCTG CGAGATGAGC        5000
CGTCTAATGA AAAGTCAGAT GTGTACAGCT TCGGGTCAT CTTGTGGGAG         5050
CTTGCTACAT TGCAACAACC ATGGGGTAAC TTAAATCCGG CTCAGGTACT        5100
TCCCACTCTA AACATCCCAA ATAATAATGA TATTATTTTG CATTTGGAAG        5150
TCCCTCACTC TACATTTCAT AACATGCTAT ATATGATCAT CCAACAAAAT        5200
GTTCCATAGG TTGTAGCTGC GGTTGGTTTC AAGTGTAAAC GGCTGGAGAT        5250
CCCGCGTAAT CTGAATCCTC AGGTTGCAGC CATAATCGAG GGTTGTTGGA       5300
CCAAGTACGT TAAGATTTTC TATCTCTTTT TTGAATTCTT CTTGAATAGA       5350
CTTCATGTTT ATGTATGTGT TTCATTACCA GTGAGCCATG GAAGCGTCCA       5400
TCATTTGCAA CTATAATGGA CTTGCTAAGA CCATTGATCA AATCAGCGGT       5450
TCCTCCGCCC AACCGCTCGG ATTTGTAAAA TACCCCCGGT CCATTCAAAA       5500
GTTGTTATAA TCATGATATG CACATATACT CTCAGCATTC TTTTGCTGCC       5550
CAGGAGGGAG ACACTAGTTA AGATATAGCT TTAAAGGTAC ATTCCTCATG       5600
AGCTATCAAT CATATCCTAC AGAATCCCAT GGTTTTATA CATGTATTAT        5650
TTTTGCGATC TTTGTCTGCTG TTTTGTTCC CTTTTTAATG TTGCAGATTG       5700
TTAAAATGTA CATGACTATT GTCACAGGGA GGAAAAAAAA ATGTAGTAAT       5750
GGAAACAATG TGAGGGATAT AATCTATCTA TCTAGTCCCA AAGGGTAAGC       5800
AATATTGTGT TGTTATGTCT TTGTAGCAAT GCACTGAAAG CTATATTTAA       5850
TTACATTGCT GTACATTTAT ACCGCTAAAT TAGTTACTAA GCGAAGGTAA       5900
AAAAGAGCAG CTGGTAAATG CTGTCAAAGG GTTTTGCAAA CTCAATATGA       5950
TTCATTGGAT TTACATTTGT TCACTGTGCG ATTAGTCTGG ACTATAAACC       6000
AACAGAAATG AAATAAGACT GTAACTTTCG GAGACTCTAA TACAGATGAA       6050
TATAATCCCA AATCGTTAAA AACGCATTGG GACTGAAAAT ATCTAGATAC       6100
ATAGTCAACT ATTTTTGCCT TCGCGTCTAA GTAAGTTCCC ACACTTGAAA       6150
ACGACTTTAC CTGTCTTCCG AATTAATCGT TTGATGGATC GGTAACCAAT       6200
AGGATTGCGT AAATCAAAAT TATACAATAT TAAATTCTGA AAAAGGAAAC       6250
ACGAAAAGCG AATCAGTGAT TTGTGAGGGC CCAGTTCCAA ATTAGAAAGC       6300
TGACCTGGCA AA                                                6312
```

( 2 ) INFORMATION FOR SEQ ID NO:7:

( i ) SEQUENCE CHARACTERISTICS:
        ( A ) LENGTH: 6312 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

| | | | | | |
|---|---|---|---|---|---:|
| TATAGTCCAT | TCTCTCACTT | TCTATTCTAA | ATATTGTGGA | CGTTATAAAG | 50 |
| GCTTTTTATT | TATTTTATGT | CGAGTTTTT | AGACTACGTA | GAGCCGAATG | 100 |
| AAAATTTCAT | GTTAGGTAT | ACGAAACTTG | GATCCAATGT | TACGGATTCA | 150 |
| GATTGGTGTA | AAAGATCAAA | TTTGATAGTA | TTTGGATTTG | ATAGGCAAGA | 200 |
| TGGTTTAGTA | TTTTACACTG | TGTATGTTCC | TCTTTTAGCT | TTGCGTTTTC | 250 |
| TACTTTCACT | ACGATACTAC | TTTTTATCTT | CCAATTTCAG | TTGCTTATCA | 300 |
| CCAAAATATG | AAATACCAAA | TTAATTGTTT | AAACAGTTTT | ATTAGCGATT | 350 |
| AAATTAGCAC | AAAACATATG | AATAGATATC | ATAGTCGAAT | ACAAAAATTA | 400 |
| GACAAATAAT | AATACACTAA | AAAACAAACT | AAATTGGAGA | ATTGTTTTGA | 450 |
| CAAAAAATAA | AAAAAATGTC | AAAGTTCCAT | AAAAAGGAGG | ACAAAAGAGG | 500 |
| AATATAACGA | AATTATCAAC | AGAAACGCAC | CGAGTAAGTT | TATTTCCTAT | 550 |
| GATAACGCAA | AAACAAAAAA | AAAATCCAAT | TCCATTAGAG | AGAGAGAGAG | 600 |
| AGAGAGAGAG | AGAGAGAGAC | TTTTTAGAA | AGTACACAAA | AAAAATGAAA | 650 |
| AACTAGAGAG | AGAAACAAGT | GGCTAGCTAG | CTCGCCAAAC | TTCTTCAACA | 700 |
| ATGGCGGTTT | CCTAGGGTTT | GATGTTTATA | TGATCGGGAA | ACTCTCTCAT | 750 |
| CTAGATCGCG | ATAACTCTCT | TTTCCATGGA | AATGCCCGGT | AGAAGATCTA | 800 |
| ATTACACTTT | GCTTAGTCAA | TTTTCTGACG | ATCAGGTGTC | AGTTTCCGTC | 850 |
| ACCGGAGCTC | CTCCGCCTCA | CTATGATTCC | TTGTCGAGCG | AAAACAGGAG | 900 |
| CAACCATAAC | AGCGGGAACA | CCGGGAAAGC | TAAGGCGGAG | AGAGGCGGAT | 950 |
| TTGATTGGGA | TCCTAGCGGT | GGTGGTGGTG | GTGATCATAG | GTTGAATAAT | 1000 |
| CAACCGAATC | GGGTTGGGAA | TAATATGTAT | GCTTCGTCTC | TAGGGTTGCA | 1050 |
| AAGGCAATCC | AGTGGGAGTA | GTTTCGGTGA | GAGCTCTTTG | TCTGGGATT | 1100 |
| ATTACATGCC | TACGCTTTCT | GCGGCGGCTA | ACGAGATCGA | ATCTGTTGGA | 1150 |
| TTTCCTCAAG | ATGATGGGTT | TAGGCTTGGA | TTTGGTGGTG | GTGGAGGAGA | 1200 |
| TTTGAGGATA | CAGATGGCGG | CGGACTCCGC | TGGAGGGTCT | TCATCTGGGA | 1250 |
| AGAGCTGGGC | GCAGCAGACG | GAGGAGAGTT | ATCAGCTGCA | GCTTGCATTG | 1300 |
| GCGTTAAGGC | TTTCGTCGGA | GGCTACTTGT | GCCGACGATC | CGAACTTTCT | 1350 |
| GGATCCTGTA | CCGGACGAGT | CTGCTTTACG | GACTTCGCCA | AGTTCAGCCG | 1400 |
| AAACCGTTTC | ACATCGTTTC | TGGGTATTTG | TTCCTGTTAA | GCTTTGTTTC | 1450 |
| CCAAAATTAT | TGAATCGTGG | TTATAGAGAT | ATGGTCCTCT | TGTTTCCGAA | 1500 |
| GTTTCAGTTA | GATCTCCTTA | CCAAAAGTCT | ATTAGTAGCA | AATGAGATAT | 1550 |
| GTTGTTTAGA | TACATTGCAG | AGTATGATTG | TTTTGTGTGC | TGCATCAGGT | 1600 |
| TAATGGCTGC | TTATCGTACT | ATGATAAAGT | TCCTGATGGG | TTTTATATGA | 1650 |
| TGAATGGTCT | GGATCCCTAT | ATTTGGACCT | TATGCATCGA | CCTGCATGAA | 1700 |

```
AGTGGTCGCA TCCCTTCAAT TGAATCATTA AGAGCTGTTG ATTCTGGTGT    1750
TGATTCTTCG CTTGAAGCGA TCATAGTTGA TAGGCGTAGT GATCCAGCCT    1800
TCAAGGAACT TCACAATAGA GTCCACGACA TATCTTGTAG CTGCATTACC    1850
ACAAAGAGG  TTGTTGATCA GCTGGCAAAG CTTATCTGCA ATCGTATGGG    1900
GTTGTACTC  ATACAATCCT TACTATCCCT TTGAACTTAT ATTTTATAT     1950
CTTCCTGTGA TTTCTCACAT TGTACTCGTT AATTCTTGCT TCCCCAGGGG    2000
TCCAGTTATC ATGGGGAAG  ATGAGTTGGT TCCATGTGG  AAGGAGTGCA    2050
TTGATGGTCT AAAAGAAATC TTTAAAGTGG TGGTTCCCAT AGGTAGCCTC    2100
TCTGTTGGAC TCTGCAGACA TCGAGCTTTA CTCTTCAAAG TGAGATCCCA    2150
ACTTTGATGC TATCCCCATG ACATTTAAGA CATCTTGTGA AATGATCATA    2200
TAAATTATTG TGCTTCATCC ATTTGTTTTT ATTGGAATAC ATATGAAGAA    2250
CGTTGAATGT GAAAAGTGGT GTTATTGATT AGAAAAAAT  AGGTTACTGA    2300
TAGTTGAATG TTCCAAAGAA AAAAGTATT  TTATATCTTC TATTTGGTGC    2350
ATGCAGGTAC TGGCTGACAT AATTGATTTA CCCTGTCGAA TTGCCAAAGG    2400
ATGTAAATAT TGTAATAGAG ACGATGCCGC TTCGTGCCTT GTCAGGTTTG    2450
GGCTTGATAG GTATGATACA AGTGATTGCG AAAGAGCCTT TATTTCCTA    2500
TTTTCTTTGC TTTTTGTTTC TGGAAAAACA ATTATAGCTC CAAATGTTTC    2550
GCAGAATATT AGGTTGATGA CGTGGAAAAT TTGTTTTGGT TTCAGGGAGT    2600
ACCTGGTTGA TTTAGTAGGA AAGCCAGGTC ACTTATGGGA GCCTGATTCC    2650
TTGCTAAATG GTCCTTCATC TATCTCAATT TCTTCTCCTC TGCGGTTTCC    2700
ACGACCAAAG CCAGTTGAAC CCGCAGTCGA TTTTAGGTTA CTAGCCAAAC    2750
AATATTTCTC CGATAGCCAG TCTCTTAATC TTGTTTTCGA TCCTGCATCA    2800
GGTATTCCCA TACAAAAAAC CTAAATAATA TGTTAACTTT TTGCATGCTG    2850
CTTACATCTC GTTTTGTATT TCCCCTAAAA GAGTAATCTC CTATCATTTA    2900
GGGTATTTCT TGATCATGTC TCAGTATCTG AAGTGTTAGT AGTCTTAGAA    2950
TGATTCTATT GTTTGTTTTC TTGTCTCTTT TCACTTTAGT TGTTTTGGC    3000
TGTTGATGTG TATGTTTGTT GGTGGGTTCT TTGCCTAATG ATATTTAAGG    3050
TTAAACTTGT TAGTCTGCTG TTCAAGCTTA TGAATTCTAG TGCATTTATG    3100
TGCAAGACTT GTCTTCTGGA CTCTAATTTC TTATATCTGC TTGTTTGAAT    3150
GGTTGTAGAT GATATGGGAT TCTCAATGTT TCATAGGCAA TATGATAATC    3200
CGGGTGGAGA GAATGACGCA TTGGCAGAAA ATGGTGGTGG GTCTTTGCCA    3250
CCCAGTGCTA ATATGCCTCC ACAGAACATG ATGCGTGCGT CAAATCAAAT    3300
TGAAGCAGCA CCTATGAATG CCCCACCAAT CAGTCAGCCA GTTCCAAACA    3350
GGGCAAATAG GGAACTTGGA CTTGATGGTG ATGATATGGA CATCCCGTGG    3400
TGTGATCTTA ATATAAAAGA AAAGATTGGA GCAGGTAATA ATTTTACGGA    3450
AAAATTAATG ATTCGGTCTA AAAATGCAAA GAAATATGAA ATTCTTGAGG    3500
AAGTGGTTTT GCTTTGGACT CTGTTCTCGA ACAAAATAAG GAAAAAGTGC    3550
CACCCATTTT GAGATTACAT TCTTCTCTGT TGCCTTTAAT TCTTCCACTC    3600
TAATTTGAGC GACTGCTCTT TCAGGTTCCT TTGGCACTGT CCACCGTGCT    3650
GAGTGGCATG GCTCGGTAAG AACTTTTTTG TCAGAATTTA CGCAGCTGAA    3700
```

| | | | | |
|---|---|---|---|---|
| TTTTTTTCG | CTCTAAAAAT | TTGGTTGTGA | CTTTTGGATC | TGCTTGGTAT | 3750 |
| TATAAAAGGC | AAAGTTATTG | TATATGTGAC | TCTCCGTTCT | GTCAGAAATT | 3800 |
| AAACACGGAC | AAAAGGTGTC | CCATTTTAGA | TGTATATGTG | TCTTTATATC | 3850 |
| ATAAATTTGT | CTTCCTGTTT | GAATTTTACA | ATTCTATCAC | TAGAAGAATT | 3900 |
| CTAATTTTGA | TTATTGCAGT | AATATTCTCT | ATCAATTTCA | GGATGTTGCT | 3950 |
| GTGAAAATTC | TCATGGAGCA | AGACTTCCAT | GCTGAGCGTG | TTAATGAGTT | 4000 |
| CTTAAGAAAG | GTGCACAAAT | AAAATTTTCT | CTTGATTTTG | GTAATGAACT | 4050 |
| TGTTGTATTA | ATGTCTCCAA | TGATCTTGAT | TCGCTGTCAG | GTTGCGATAA | 4100 |
| TGAAACGCCT | TCGCCACCCT | AACATTGTTC | TCTTCATGGG | TGCGGTCACT | 4150 |
| CAACCTCCAA | ATTTGTCAAT | AGTGACAGAA | TATTTGTCAA | GGTACAATTA | 4200 |
| CTTGGATTTG | GAAGGTTTGA | TGTACTGAGT | GTAGAATTTT | GGCCTATAAT | 4250 |
| GACTCTAATA | CCATGATTTC | TTTCAAACAG | AGGTAGTTTA | TACAGACTTT | 4300 |
| TGCATAAAAG | TGGAGCAAGG | GAGCAATTAG | ATGAGAGACG | TCGCCTGAGT | 4350 |
| ATGGCTTATG | ATGTGGTATG | TTTAACTCCT | TATGTTACAT | GTATGGGTGA | 4400 |
| TTACTTCCTG | ATCTTGGTGT | TTCTTCACAT | GGAACTTTCT | TTCCAATTCT | 4450 |
| CTGTCACAGG | CTAAGGGAAT | GAATTATCTT | CACAATCGCA | ATCCTCCAAT | 4500 |
| TGTGCATAGA | GATCTAAAAT | CTCCAAACTT | ATTGGTTGAC | AAAAAATATA | 4550 |
| CAGTCAAGGT | TTGAATCTAA | ATTAGAAATT | GTTGTGTCCA | ATGTTTTGAT | 4600 |
| TTTGATATTT | TATTCCTCTT | GTGAGACAAG | CTTATATATA | AATTATGATT | 4650 |
| TTTAATTCTA | AATTGGTTTG | GAGACATTAC | AAAAAGGCGT | TAATCTGCTG | 4700 |
| AAACTTAAAA | GATACAGCAG | CCTCAAGCTG | TCGTCTTAAA | AACAATCAGA | 4750 |
| ACATTATTAT | TCTAACTCCT | CAATTTGTCT | TGAAATTTCA | GGTTTGTGAT | 4800 |
| TTTGGTCTCT | CGCGATTGAA | GGCCAGCACG | TTTCTTTCCT | CGAAGTCAGC | 4850 |
| AGCTGGAACC | GTAAGTTCAG | TTTGTTTGAA | ACTAAAACAC | GCTGAACAAC | 4900 |
| GTAACTTTCT | TCTAGGTCCT | ATTTCCAATG | GAAGCTAAAT | AATTACTGAC | 4950 |
| TTTGATATAT | CAGCCCGAGT | GGATGGCACC | AGAAGTCCTG | CGAGATGAGC | 5000 |
| CGTCTAATGA | AAAGTCAGAT | GTGTACAGCT | TCGGGGTCAT | CTTGTGGGAG | 5050 |
| CTTGCTACAT | TGCAACAACC | ATGGGGTAAC | TTAAATCCGG | CTCAGGTACT | 5100 |
| TCCCACTCTA | AACATCCCAA | ATAATAATGA | TATTATTTTG | CATTTGGAAG | 5150 |
| TCCCTCACTC | TACATTTCAT | AACATGCTAT | ATATGATCAT | CCAACAAAAT | 5200 |
| GTTCCATAGG | TTGTAGCTGC | GGTTGGTTTC | AAGTGTAAAC | GGCTGGAGAT | 5250 |
| CCCGCGTAAT | CTGAATCCTC | AGGTTGCAGC | CATAATCGAG | GGTTGTTGGA | 5300 |
| CCAAGTACGT | TAAGATTTTC | TATCTCTTTT | TTGAATTCTT | CTTGAATAGA | 5350 |
| CTTCATGTTT | ATGTATGTGT | TTCATTACCA | GTGAGCCATG | GAAGCGTCCA | 5400 |
| TCATTTGCAA | CTATAATGGA | CTTGCTAAGA | CCATTGATCA | AATCAGCGGT | 5450 |
| TCCTCCGCCC | AACCGCTCGG | ATTTGTAAAA | TACCCCGGT | CCATTCAAAA | 5500 |
| GTTGTTATAA | TCATGATATG | CACATATACT | CTCAGCATTC | TTTTGCTGCC | 5550 |
| CAGGAGGGAG | ACACTAGTTA | AGATATAGCT | TTAAAGGTAC | ATTCCTCATG | 5600 |
| AGCTATCAAT | CATATCCTAC | AGAATCCCAT | GGTTTTTATA | CATGTATTAT | 5650 |
| TTTTGCGATC | TTTGTCTGCTG | TTTTGTTCC | CTTTTAATG | TTGCAGATTG | 5700 |

| | | | | | |
|---|---|---|---|---|---|
| TTAAAATGTA | CATGACTATT | GTCACAGGGA | GGAAAAAAAA | ATGTAGTAAT | 5750 |
| GGAAACAATG | TGAGGGATAT | AATCTATCTA | TCTAGTCCCA | AAGGGTAAGC | 5800 |
| AATATTGTGT | TGTTATGTCT | TTGTAGCAAT | GCACTGAAAG | CTATATTTAA | 5850 |
| TTACATTGCT | GTACATTTAT | ACCGCTAAAT | TAGTTACTAA | GCGAAGGTAA | 5900 |
| AAAAGAGCAG | CTGGTAAATG | CTGTCAAAGG | GTTTTGCAAA | CTCAATATGA | 5950 |
| TTCATTGGAT | TTACATTTGT | TCACTGTGCG | ATTAGTCTGG | ACTATAAACC | 6000 |
| AACAGAAATG | AAATAAGACT | GTAACTTTCG | GAGACTCTAA | TACAGATGAA | 6050 |
| TATAATCCCA | AATCGTTAAA | AACGCATTGG | GACTGAAAAT | ATCTAGATAC | 6100 |
| ATAGTCAACT | ATTTTTGCCT | TCGCGTCTAA | GTAAGTTCCC | ACACTTGAAA | 6150 |
| ACGACTTTAC | CTGTCTTCCG | AATTAATCGT | TTGATGGATC | GGTAACCAAT | 6200 |
| AGGATTGCGT | AAATCAAAAT | TATACAATAT | TAAATTCTGA | AAAAGGAAAC | 6250 |
| ACGAAAAGCG | AATCAGTGAT | TTGTGAGGGC | CCAGTTCCAA | ATTAGAAAGC | 6300 |
| TGACCTGGCA | AA | | | | 6312 |

( 2 ) INFORMATION FOR SEQ ID NO:8:

( i ) SEQUENCE CHARACTERISTICS:
        ( A ) LENGTH: 13 amino acid residues
        ( B ) TYPE: amino acid
        ( C ) STRANDEDNESS:
        ( D ) TOPOLOGY: unknown ( i i ) MOLECULE TYPE:

( x i ) SEQUENCE DESCRIPTION: SEQ ID NO:8:

Ile Val His Arg Asp Leu Lys Ser Pro Asn Leu Leu Val
1               5                   10

( 2 ) INFORMATION FOR SEQ ID NO:9:

( i ) SEQUENCE CHARACTERISTICS:
        ( A ) LENGTH: 9 amino acid residues
        ( B ) TYPE: amino acid
        ( C ) STRANDEDNESS:
        ( D ) TOPOLOGY: unknown ( i i ) MOLECULE TYPE:

( x i ) SEQUENCE DESCRIPTION: SEQ ID NO:9:

Ile Gly Ala Gly Ser Phe Gly Thr Val
1               5

( 2 ) INFORMATION FOR SEQ ID NO:10:

( i ) SEQUENCE CHARACTERISTICS:
        ( A ) LENGTH: 8 amino acid residues
        ( B ) TYPE: amino acid
        ( C ) STRANDEDNESS:
        ( D ) TOPOLOGY: unknown ( i i ) MOLECULE TYPE:

( x i ) SEQUENCE DESCRIPTION: SEQ ID NO:10:

His Arg Asp Leu Lys Ser Pro Asn
1               5

( 2 ) INFORMATION FOR SEQ ID NO:11:

( i ) SEQUENCE CHARACTERISTICS:
        ( A ) LENGTH: 8 amino acid residues
        ( B ) TYPE: amino acid

```
             ( C ) STRANDEDNESS:
             ( D ) TOPOLOGY: unknown ( i i ) MOLECULE TYPE:

( x i ) SEQUENCE DESCRIPTION: SEQ ID NO:11:

Thr  Pro  Glu  Trp  Met  Ala  Pro  Glu
  1                 5

( 2 ) INFORMATION FOR SEQ ID NO:12:

( i ) SEQUENCE CHARACTERISTICS:
                ( A ) LENGTH: 8 amino acid residues
                ( B ) TYPE: amino acid
                ( C ) STRANDEDNESS:
                ( D ) TOPOLOGY: unknown ( i i ) MOLECULE TYPE:

( x i ) SEQUENCE DESCRIPTION: SEQ ID NO:12:

Gly  Xaa  Xaa  Xaa  Xaa  Gly  Lys  Ser
  1                 5

( 2 ) INFORMATION FOR SEQ ID NO:13:

( i ) SEQUENCE CHARACTERISTICS:
                ( A ) LENGTH: 8 amino acid residues
                ( B ) TYPE: amino acid
                ( C ) STRANDEDNESS:
                ( D ) TOPOLOGY: unknown ( i i ) MOLECULE TYPE:

( x i ) SEQUENCE DESCRIPTION: SEQ ID NO:13:

Gly  Xaa  Xaa  Xaa  Xaa  Gly  Lys  Thr
  1                 5
```